US012582714B2

(12) United States Patent
Zhou et al.

(10) Patent No.: US 12,582,714 B2
(45) Date of Patent: Mar. 24, 2026

(54) METHODS AND COMPOSITIONS FOR FREEZING AND THAWING MAMMALIAN CELLS

(71) Applicant: TAKEDA PHARMACEUTICAL COMPANY LIMITED, Osaka (JP)

(72) Inventors: Shuxia Zhou, Cambridge, MA (US); Lan Cao, Cambridge, MA (US); Dayong Gao, Cambridge, MA (US); Qiong Xue, Cambridge, MA (US); Jiusong Sun, Cambridge, MA (US); Huang Zhu, Cambridge, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 31 days.

(21) Appl. No.: 18/361,787

(22) Filed: Jul. 28, 2023

(65) Prior Publication Data

US 2024/0050566 A1 Feb. 15, 2024

Related U.S. Application Data

(63) Continuation of application No. PCT/US2022/015870, filed on Feb. 9, 2022.
(Continued)

(51) Int. Cl.
*A61K 40/15* (2025.01)
*A01N 1/162* (2025.01)
(Continued)

(52) U.S. Cl.
CPC .............. *A61K 40/15* (2025.01); *A01N 1/162* (2025.01); *A61K 40/31* (2025.01); *A61P 35/00* (2018.01);
(Continued)

(58) Field of Classification Search
CPC .................................................... A61K 35/17
See application file for complete search history.

(56) References Cited

U.S. PATENT DOCUMENTS 6,136,525 A 10/2000 Mullon et al.
9,821,012 B2 11/2017 Wu et al.
(Continued)

FOREIGN PATENT DOCUMENTS

JP 2018/502114 A 1/2018
JP 6876004 B2 * 5/2021 ........... A01N 1/0221
(Continued)

OTHER PUBLICATIONS

Liu et al. (Leukemia. Feb. 2018; 32 (2): 520-531).*
(Continued)

*Primary Examiner* — Thomas J. Visone
(74) *Attorney, Agent, or Firm* — Proskauer Rose LLP

(57) ABSTRACT

The present disclosure provides, among other things, a method of cryopreserving and thawing cells that results in the thawed cells having high cellular viability and functionality post-thawing. In some embodiments, a large-scale method of cryopreserving cells is provided, the method comprising: (a) contacting the cells with a cryopreservation medium; (b) cooling the cells to −80° C. at a controlled rate to minimize latent heat of fusion; and (c) storing the cells in liquid nitrogen vapor phase, thereby cryopreserving the immune cells.

6 Claims, 15 Drawing Sheets

Specification includes a Sequence Listing.

Related U.S. Application Data

(60) Provisional application No. 63/147,737, filed on Feb. 9, 2021.

(51) Int. Cl.

| | |
|---|---|
| *A61K 40/31* | (2025.01) |
| *A61P 35/00* | (2006.01) |
| *C12N 5/0783* | (2010.01) |

(52) U.S. Cl.
CPC ........ *C12N 5/0646* (2013.01); *A61K 2239/13* (2023.05); *A61K 2239/21* (2023.05); *A61K 2239/25* (2023.05); *C12N 2510/00* (2013.01)

(56) References Cited

U.S. PATENT DOCUMENTS

| | | | |
|---|---|---|---|
| 10,246,505 B2 | 4/2019 | Berger et al. | |
| 2011/0206776 A1* | 8/2011 | Tom ........................ | A61P 43/00 424/583 |
| 2019/0000070 A1* | 1/2019 | De Larichaudy ...... | A61K 38/38 |
| 2019/0330592 A1 | 10/2019 | Hariri et al. | |

FOREIGN PATENT DOCUMENTS

| | | | |
|---|---|---|---|
| WO | 2015/155187 A1 | 10/2015 | |
| WO | 2016063208 A1 | 4/2016 | |
| WO | 2016/109668 A1 | 7/2016 | |
| WO | 2018/079497 A1 | 5/2018 | |
| WO | 2019/213610 A1 | 11/2019 | |
| WO | WO2020043670 A1 * | 3/2020 | |
| WO | WO-2022129692 A1 * | 6/2022 | ..... A61K 39/001106 |
| WO | WO-2023019229 A1 * | 2/2023 | |

OTHER PUBLICATIONS

Rudikoff et al. (Proc. Natl. Acad. Sci. USA. 1982; 79: 1979-1983).*
Mariuzza et al. (Annu. Rev. Biophys. Biophys. Chem. 1987; 16: 139-159).*
Winkler et al. (J. Immunol. Oct. 15, 2000; 165 (8): 4505-4514).*
Gussow et al. (Methods in Enzymology. 1991; 203: 99-121).*
Giusti et al. (Proc. Natl. Acad. Sci. USA. May 1987; 84 (9): 2926-30).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205.*
MacCallum et al. (J. Mol. Biol. Oct. 11, 1996; 262 (5): 732-745).*
Holm et al. (Mol. Immunol. Feb. 2007; 44 (6): 1075-1084).*
Bridgeman et al. (J.Immunol. Jun. 15, 2010; 184 (12): 6938-49).*
Hudecek et al. (Clin. Cancer Res. Jun. 15, 2013; 19 (12): 3153-64).*
Lazar et al. (Mol. Cell. Biol. 1988, 8: 1247-52).*
Burgess et al. (J. Cell Biol. 1990; 111: 2129-38).*
Teplyakov et al. (Proteins. May 2018; 86 (5): 495-500).*
Parker et al. (eNeuro. Sep.-Oct. 2018; 5 (5): e0135-18.2018; pp. 1-21).*
Solocinski et al. (Cryobiology. Apr. 2017: 75: 134-43).*

Limaye et al. (J. Hematother. Stem Cell Res. Oct. 2001; 10 (5): 709-18).*
Shinde et al. (Transfusion. Feb. 2019; 59 (2): 686-96).*
Pasha et al. (Transfusion. Jul. 2017; 57 (7): 1744-1754).*
Braudeau et al. (Cytometry B Clin. Cytom. Nov. 2021; 100 (6): 652-65).*
Damodharan et al. (Cytotherapy. Aug. 2020; 22 (8): 450-457; author manuscript; pp. 1-23).*
Asnani et al. (Leukemia. Apr. 2020; 34 (4): 1202-7).*
Van Zelm et al. (N. Engl. J. Med. May 4, 2006; 354 (18): 1901-12).*
Tedder et al. (J. Immunol. Jul. 15, 1989; 143 (2): 712-7).*
Nagorsen et al. (Pharmacol. Ther. Dec. 2012; 136 (3): 334-42).*
Gmyrek et al. (Cell Immunol. Sep. 2017; 319: 28-34; author manuscript; pp. 1-17).*
Carson et al. (J. Exp. Med. Oct. 1, 1994; 180 (4): 1395-403).*
Chiang et al. (J. Transl. Med. Nov. 14, 2011; 9: 198; pp. 1-16).*
Stoiber et al. (Cells. May 17, 2019; 8 (5): 472; pp. 1-26).*
Shinde et al. (Transfusion. Feb. 2019; 59 (2): 686-696).*
Rui et al. (Cytotherapy. Aug. 12, 2019; 21 (9): 943-57; author manuscript, pp. 1-25).*
Cloutier et al. (Transfusion. Jul. 2016; 56 (7): 1786-91).*
Takeda Pharmaceuticals Co.; Human Albumin Solution IP 5%, 20% & 25%; https://content.takeda.com/?contenttype=PI&product=HUM_AL&language=ENG&country=IND&documentnumber=2; accessed Jan. 17, 2024; pp. 1-3.*
U.S. Appl. No. 18/274,988, filed Jul. 28, 2023, Zhou.*
U.S. Appl. No. 18/361,790, filed Jul. 28, 2023, Zhou.*
"PlasmaLyte A: Balanced Salt Solution," Baxter (Year: 2025).*
"Optimal Cryopreservation Conditions to Preserve Viability, Proliferation and Lytic Function of . . ." Cobanoglu et al., University of Texas MD Anderson Cancer Center, Abstracts, Biol Blood Marrow Transplant 20 (2014) S128-S150 (Year: 2014).*
International Search Report for PCT/US2022/015626 dated May 11, 2022 (4 pages).
International Search Report for PCT/US2022/015627 dated May 20, 2022 (4 pages).
International Search Report for PCT/US2022/015869 dated May 20, 2022 (4 pages).
International Search Report for PCT/US2022/015870 dated May 27, 2022 (4 pages).
Brockbank, Kelvin G.M., et al., "Chapter 8: Tissue Preservation", Advances in Biopreservation, Eds. Baust et al., CRC Press, 2006, pp. 157-196, Retrieved from URL: https://www.andrew.cmu.edu/user/yr25/TaylorPublications/MJTaylor108.pdf (40 pages).
Freshney, R. Ian , et al., "Chapter 15—Cryopreservation and Banking", Culture of Animal Cells: A Manual of Basic Technique and Specialized Applications, 7th Edition, John Wiley & Sons, Inc., 2015, pp. 307-327, (20 pages).
Liu, E , et al., "Cord blood NK cells engineered to express IL-15 and a CD19-targeted CAR show long-term persistence and potent antitumor activity", Leukemia, vol. 32, 2018, pp. 520-531, DOI: 10.1038/leu.2017.226 (12 pages).
Pomeroy, et al., "A Genetically Engineered Primary Human Natural Killer Cell Platform for Cancer Immunotherapy", Molecular Therapy vol. 28, No. 1, 2019 The American Society of Gene and Cell Therapy, Jan. 2020 (12 pages).
Battram, et al. "BCMA-Targeting CAR-T Cells Expanded in IL-15 have an Improved Phenotype for Therapeutic use Compared to Those Grown in IL-2 or IL-15/IL-7" (abstract), Journal for ImmunoTherapy of Cancer, Cellular Therapies, Nov. 9, 2020, 8: Supplement 3 http://jitc.bmj.com; A65 (1 page).

\* cited by examiner

| Reportable Marker | CAR-NK-1 16 mL fill | CAR-NK-2 30 mL fill | CAR-NK-3 45 mL fill | CAR-NK-4 1 mL fill | CAR-NK-5 16 mL fill | CAR-NK-6 30 mL fill | CAR-NK-7 45 mL fill | CAR-NK-8 1 mL fill | CAR-NK -Fresh | CAR-NK-2ml Cryovial |
|---|---|---|---|---|---|---|---|---|---|---|
| Live Population (7AAD-) | 41.87 | 42.66 | 46.43 | 47.01 | 46.65 | 43.86 | 48.96 | 42.41 | 53.61 | 40.80 |
| CD56-CD48+CD32+ | 0.00 | 0.00 | 0.01 | 0.00 | 0.00 | 0.00 | 0.00 | 0.00 | 0.00 | 0.00 |
| CD56+CD3- | 97.84 | 97.90 | 98.31 | 97.51 | 97.10 | 98.05 | 98.06 | 95.96 | 98.08 | 98.14 |
| CD3+ | 0.05 | 0.07 | 0.01 | 0.12 | 0.09 | 0.07 | 0.06 | 0.10 | 0.05 | 0.05 |
| F(ab')2+(NK-CAR)+ | 50.64 | 49.07 | 50.48 | 48.20 | 50.50 | 50.19 | 51.25 | 48.60 | 1.51 | 47.93 |

FIG. 7B

| Sample | Container | Cell conc. | Fill vol (ml) | Formulation | % Killing @ E:T=10:1 | Viability (%) |
|---|---|---|---|---|---|---|
| CAR-NK-DP1 | 50 mL AT vial | 6 M/mL | 35 | 40% Plasmalyte+10%HS A+50%CS10 | 93.01 | 97.3 |
| CAR-NK-DP2 | 2 mL AT vial | 80 M/mL | 1 | | 92.77 | 97.2 |
| CAR-NK-DP3 | 2 mL AT vial | 6 M/mL | 1 | | 89.76 | 96.6 |
| CAR-NK-DP4 | 50 mL AT vial | 6 M/mL | 35 | 40% Plasmalyte+10%HS A+50%CS10+30 mM trehalose | 92.17 | 97.7 |
| CAR-NK-DP5 | 2 mL AT vial | 80 M/mL | 1 | | 92.77 | 97.6 |
| CAR-NK-DP6 | 2 mL AT vial | 6 M/mL | 1 | | 91.69 | 98.3 |

FIG. 8B

| Reportable Marker | CAR-NK 3-1 | CAR-NK 3-2 | CAR-NK 3-3 | CAR-NK 3-4 | CAR-NK 3-5 | CAR-NK 3-6 |
|---|---|---|---|---|---|---|
| Live Population (7AAD-) | 62.86 | 64.71 | 62.68 | 64.82 | 63.82 | 60.90 |
| CD56-CD48+CD32+ | 0.00 | 0.00 | 0.00 | 0.00 | 0.00 | 0.00 |
| CD56+CD3- | 99.35 | 99.54 | 99.55 | 99.57 | 99.59 | 99.56 |
| CD3+ | 0.09 | 0.07 | 0.11 | 0.12 | 0.12 | 0.12 |
| F(ab')2+(NK-CAR)+ | 72.45 | 72.82 | 72.28 | 72.98 | 72.55 | 73.19 |

FIG. 8C

METHODS AND COMPOSITIONS FOR FREEZING AND THAWING MAMMALIAN CELLS

CROSS-REFERENCE TO RELATED APPLICATIONS

This application is a continuation of International Application No. PCT/US2022/015870 filed Feb. 9, 2022, which claims priority to U.S. Provisional Patent Application Ser. No. 63/147,737, filed on Feb. 9, 2021, and PCT/US2022/015627, filed Feb. 8, 2022, the contents of each of which are herein incorporated by reference in their entireties for all purposes.

INCORPORATION BY REFERENCE OF SEQUENCE LISTING

The present specification makes reference to a Sequence Listing submitted electronically as a ST26 XML file named "MIL-012US1_SL". The XML file was generated Jul. 28, 2023 and is 1,048,576 bytes in size. The entire contents of the Sequence Listing are herein incorporated by reference in their entirety.

BACKGROUND

Cryopreservation of biological material such as e.g. cells, tissue, organs, blood products, embryos, sperm, stem cells, fish eggs, etc., entails freezing a biological material to low enough temperatures, such that chemical processes, which might otherwise damage the material are halted thereby preserving the material.

The field of cryopreservation often aims to not only freeze the biological materials, but also to retain their viability, i.e. their ability to resume normal biological function after thawing. When freezing a biological material, the fluid inside generally undergoes a phase transition during which ice crystals may form. The formation of ice crystals can cause damage to the biological material, such that it may not be viable after thawing.

Therefore, optimization of cryopreservation conditions is desirable, especially when cryopreserving cells used for therapy, for ensuring survival of cells that may need to be shipped for use in various applications, such as for cellular therapy, regenerative medicine, tissue engineering, and many other biomedical applications.

Suboptimal cryopreservation can lead to batch-to-batch variation in cellular viability and functionality, reduced cell yield, and also to the potential selection of subpopulations with genetic or epigenetic characteristics divergent from the original cells. Regulatory requirements also have an impact on cryopreservation as these will require a robust and reproducible approach to the freezing, storage and thawing of the product.

SUMMARY

The present application is based, at least in part, on methods and compositions for the effective freezing and thawing of mammalian cells. The present invention is based, in part, on the development of a large-scale cryopreservation/thawing method that is generally applicable to mammalian cells, for example to immune cells, and in particular engineered immune cells suitable for cell therapy. This application discloses a freezing method comprising various cooling, heating and holding steps that allows for the cryopreservation of cells that have high viability and function post-thawing. Further, the freeze/thaw methods described herein enable consistent freezing of a cell containing sample at a large scale (e.g., greater than 10 mL in volume) in less than or about 60 minutes as well as enable direct administration of the subsequently thawed cell sample to a subject in need thereof, as described herein.

For example, as described in more detail below, the methods described herein allow for the retention of immune cell function in vitro and in vivo at least comparable to freshly isolated cells. Furthermore, the methods and compositions provided herein could be used to preserve large volumes of immune cells, especially allogeneic engineered immune cells suitable for cell therapy, for example for storage and transport to cell banks or hospitals where the cells can be used for further culture and analyses or can be injected directly into a patient in need thereof. Thus, the present application provides freezing and thawing methods that can be highly effective in preservation of large volume of mammalian cells and in particular, engineered immune cells suitable for cell therapy.

In some aspects, a large-scale method of cryopreserving immune cells is provided, the method comprising: (a) providing a container comprising a sample comprising immune cells suspended in a cryopreservation medium, wherein the sample volume is at least 5 percent less than the full capacity volume of the container, and wherein the sample volume is at least 10 ml; (b) cooling the container from a temperature above freezing temperature of the sample to a temperature of about or below –80° C. in a multi-step process at a controlled rate to minimize latent heat of fusion; and (c) storing the cells in liquid nitrogen vapor phase, thereby cryopreserving the immune cells.

In some embodiments, the controlled rate to minimize latent heat of fusion comprises two or more steps of reducing the temperature at a rate between 0.75° C. per minute to 30° C. per minute, to a final temperature of –80° C. or below.

In some embodiments, the total time for achieving cryopreservation of the immune cells is less than 120 minutes, less than 110 minutes, less than 100 minutes, less than 90 minutes, less than 80 minutes, less than 70 minutes or less than 60 minutes. Accordingly, in some embodiments, the total time for achieving cryopreservation of the immune cells is less than 120 minutes. In some embodiments, the total time for achieving cryopreservation of the immune cells is less than 110 minutes. In some embodiments, the total time for achieving cryopreservation of the immune cells is less than 100 minutes. In some embodiments, the total time for achieving cryopreservation of the immune cells is less than 90 minutes. In some embodiments, the total time for achieving cryopreservation of the immune cells is less than 80 minutes. In some embodiments, the total time for achieving cryopreservation of the immune cells is less than 70 minutes. In some embodiments, the total time for achieving cryopreservation of the immune cells is less than 60 minutes.

In some embodiments, the immune cells are freshly isolated or at least once-frozen and thawed.

In some embodiments, the immune cells are naturally occurring or engineered natural killer (NK) cells, alpha beta T cells, gamma delta T cells, regulatory T cells (Tregs), induced pluripotent stem cells (iPSCs), iPSC derived T or NK cells, hematopoietic stem cells (HSCs), mesenchymal stromal cells (MSCs), dendritic cells, macrophages or B cells. Accordingly, in some embodiments, the immune cells are naturally occurring or engineered NK cells. In some embodiments, the immune cells are engineered NK cells. In some embodiments, the immune cells are alpha beta T cells. In some embodiments, the immune cells are gamma delta. In some embodiments, the immune cells are Tregs. In some embodiments, the immune cells are iPSC. In some embodiments, the immune cells are iPSC derived T cells. In some embodiments, the immune cells are iPSC derived NK cells. In some embodiments, the immune cells are HSCs. In some embodiments, the immune cells are MSCs. In some embodiments, the immune cells are dendritic cells. In some embodiments, the immune cells are macrophages. In some embodiments, the immune cells are B cells.

In some embodiments, the immune cells are cord blood derived NK cells engineered with a chimeric antigen receptor (CAR).

In some embodiments, the NK cells comprise a chimeric antigen receptor (CAR). The NK cell can comprise any CAR, including for example one or more of a CD19 CAR, B cell maturation antigen (BCMA) CAR, glypican-3 (GPC3) CAR, CD22 CAR, mesothelin CAR, MUC1 CAR, epithelial cell adhesion molecule (EpCAM) CAR, epidermal growth factor receptor (EGFR) CAR, CD123 CAR, CD20 CAR, HER2 CAR, GD2 CAR, CD133 CAR, EphA2 CAR, and a prostate-specific membrane antigen (PSMA) CAR. Accordingly, in some embodiments, the NK cells comprise a CD19 CAR. In some embodiments, the NK cells comprise a BCMA CAR. In some embodiments, the NK cells comprise a GPC3 CAR. In some embodiments, the NK cells comprises a CD22 CAR. In some embodiments, the NK cells comprise a mesothelin CAR. In some embodiments, the NK cells comprise a MUC1 CAR. In some embodiments, the NK cells comprise an EpCAM CAR. In some embodiments, the NK cells comprise an EGFR CAR. In some embodiments, the NK cells comprise a CD123 CAR. In some embodiments, the NK cells comprise a CD20 CAR. In some embodiments, the NK cells comprise a HER2 CAR. In some embodiments, the NK cells comprise a GD2 CAR. In some embodiments, the NK cells comprise a CD133 CAR. In some embodiments, the NK cells comprise a EphA2 CAR. In some embodiments, the NK cells comprise a PSMA CAR.

In some embodiments, the NK cells are engineered to express one or more cytokines. In some embodiments, the NK cells are engineered to express one or more of IL-15, complex of IL-15 and IL-15Rα, IL-18, IL-12, IL-7, CCL1. Accordingly, in some embodiments, the NK cells are engineered to express IL-15. In some embodiments, the NK cells are engineered to express a complex of IL-15 and IL-15Rα. In some embodiments, the NK cells are engineered to express IL-18. In some embodiments, the NK cells are engineered to express IL-12. In some embodiments, the NK cells are engineered to express IL-7. In some embodiments, the NK cells are engineered to express CCL19.

In some embodiments, the NK cells are engineered to express one or more suicide genes. For example, in some examples the NK cells are engineered to express one or more of iCaspase9, non-secretable TNFalpha, herpes simplex virus thymidine kinase (HSV-TK), Uracil phosphoribosyl transferase (UPRTase), Cytosine deaminase (CD). Accordingly, in some embodiments, the NK cells are engineered to express one or more of iCaspase9. In some embodiments, the NK cells are engineered to express non-secretable TNFalpha. In some embodiments, the NK cells are engineered to express herpes simplex virus thymidine kinase (HSV-TK). In some embodiments, the NK cells are engineered to express Uracil phosphoribosyl transferase (UPRTase). In some embodiments, the NK cells are engineered to express Cytosine deaminase (CD).

In some embodiments, the NK cells are engineered to express CD19 CAR, IL-15, and iCaspase9.

In some embodiments, NK cells are genetically engineered cord blood NK cells including a CD19-CAR comprising an anti-CD19 binding domain, a transmembrane domain such as the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154 and an intracellular signaling domain such as an intracellular signaling domain FcR gamma, FcR beta, CD3 gamma, CD3 delta, CD3-zeta, CD3 epsilon, CD5, CD22, CD79a, CD79b, and CD66d. The CD-19 binding domain can be a single chain antibody or single chain antibody fragment, such as an scFv. In one embodiment, the anti-CD19 binding domain comprises a light chain variable region comprising the amino acid sequence set forth in SEQ ID NO: 1 and/or a heavy chain variable region comprising the amino acid sequence set forth in SEQ ID NO: 2. In another embodiment, the CD-19 CAR can include an anti-CD19 binding domain, a CD28 transmembrane domain (an exemplary CD28 transmembrane sequence is shown in SEQ ID NO: 3, a CD3z signaling domain (an exemplary CD3z sequence is shown in SEQ ID NO: 4 and can further include a suicide switch such as iCaspase9 and/or IL-15.

In one embodiment, the genetically engineered cord blood NK cells include a nucleic acid molecule encoding the heavy chain variable region of an anti-CD19 binding domain and/or a nucleic acid molecule encoding the light chain variable region of an anti-CD19 binding domain.

In some embodiments, the full capacity volume of a container is about 50 ml.

In some embodiments, the full capacity volume of container is about 50 ml and the sample volume is less than 40 ml.

In some embodiments, the sample volume is about 10 ml, about 15 ml, about 20 ml, about 25 ml, about 30 ml, about 31 ml, about 32 ml, about 33 ml, about 34 ml, about 35 ml, about 36 ml, about 37 ml, about 38 ml, about 39 ml, about 40 ml, about 41 ml, about 42 ml, about 43 ml, about 44 ml or about 45 ml. Accordingly, in some embodiments, the sample volume is about 10 mL. In some embodiments, the sample volume is about 15 mL. In some embodiments, the sample volume is about 20 mL. In some embodiments, the sample volume is about 15 mL. In some embodiments, the sample volume is about 25 mL. In some embodiments, the sample volume is about 30 mL. In some embodiments, the sample volume is about 35 mL. In some embodiments, the sample volume is about 40 mL. In some embodiments, the sample volume is about 45 mL.

In some embodiments, the/container is a cryovial or a cryobag. Accordingly, in some embodiments, the container is a cryovial. In some embodiments, the container is a cryobag.

In some embodiments, the cryovial has an interior dimension of between 10 mm and 18 mm. In some embodiments, the cryovial has an exterior dimension between 15 mm and 40 mm.

In some embodiments, the cryovial has an interior dimension of about 13.5 mm.

In some embodiments, the cryovial has a height of between about 40 mm and 50 mm. In some embodiments, the cryovial has a height between about 30 mm and 90 mm.

In some embodiments, the cryovial has a height of about 48.3 mm.

In some embodiments, the container is resistant to DMSO.

In some embodiments, the immune cells are ae present at concentration of between about 6 and 120 million cells per mL. In some embodiments, the immune cells are present at a concentration of between about 6 and 25 million cells per mL.

In some embodiments, the cryopreservation medium comprises cryoprotectant, an albumin, a disaccharide and a non-pyrogenic and isotonic crystalloid solution In some embodiments, the cryopreservation medium comprises human serum albumin (HSA), sodium chloride, sodium gluconate, sodium acetate trihydrate, potassium chloride, magnesium chloride, dimethyl sulfoxide (DMSO), and a trehalose In some aspects, a large-scale method of thawing cryopreserved immune cells is provided, the method comprising: (a) heating a water bath to a temperature ranging from 37° C. and 70° C.; (b) transferring a container comprising cryopreserved immune cells to the pre-heated water bath; and (c) agitating the container at a speed of between about 100 and about 250 RPM for a suitable period of time, thereby to obtain thawed immune cells. In some embodiments, the water bath temperature is between 55° C. and 65° C. In some embodiments, the agitating the container is at a speed between about 100 and 150 RPM.

In some embodiments, the suitable period of time is between 5-15 minutes.

In some embodiments, the suitable period of time is for about 10 minutes.

In some embodiments, the agitating occurs in an orbital-shaker water bath.

In some embodiments, agitating the cells in the orbital-shaker water bath is at a speed of about 120-150 RPM.

In one embodiment, the cells are agitated at 125 RPM in a 60° C. water bath for about 10 minutes.

In some embodiments, the orbital-shaker water bath has a temperature of about 50° C., 55° C., 60° C., 65° C., 70° C., or 75° C. Accordingly, in some embodiments, the orbital-shaker water bath has a temperature of about 50° C. In some embodiments, the orbital-shaker water bath has a temperature of about 55° C. In some embodiments, the orbital-shaker water bath has a temperature of about 60° C. In some embodiments, the orbital-shaker water bath has a temperature of about 65° C. In some embodiments, the orbital-shaker water bath has a temperature of about 70° C. In some embodiments, the orbital-shaker water bath has a temperature of about 75° C.

In some embodiments, the container has a full capacity volume of about 50 mL and a sample volume between about 8 mL and 45 mL.

In some embodiments, the thawed immune cells have a post-thaw viability of 90%, 95%, 97% or more. Accordingly, in some embodiments, the thawed immune cells have a post-thaw viability of 90%. In some embodiments, the thawed immune cells have a post-thaw viability of 95%. In some embodiments, the thawed immune cells have a post-thaw viability of 97%. In some embodiments, the thawed immune cells have a post-thaw viability of more than 97%.

In some embodiments, the thawed immune cells retain in vitro and/or in vivo function similar to that of freshly isolated immune cells.

In some embodiments, the method further comprises the step of administering the thawed immune cells to a subject in need thereof.

In some aspects, a method is provided of changing temperature of a sample containing immune cells from a first temperature above the freezing temperature of the sample to a final temperature of less than or equal to −80° C., thereby cryopreserving the sample at the final temperature, the method comprises the steps of: (a) placing the sample at a first temperature above the freezing temperature of the sample; (b) reducing the first temperature to a second temperature at a first controlled rate, where the second temperature is at least 2° C. less than the first temperature; (c) reducing the second temperature to a third temperature at a second controlled rate, where the third temperature is at least 40° C. less than the second temperature; (d) increasing the third temperature to a fourth temperature at a third controlled rate, where the fourth temperature is at least 20° C. more than the third temperature; (e) reducing the fourth temperature to a fifth temperature at a fourth controlled rate, where the fifth temperature is at least 10° C. less than the fourth temperature; and (f) reducing the fifth temperature to the final temperature at a fifth controlled rate, where the final temperature is less than or equal to −80° C.

In some embodiments, the first temperature is about 4° C. to 1° C. In some embodiments, the first temperature is about 4° C. In some embodiments, the first temperature is about 3° C. In some embodiments, the first temperature is about 2° C. In some embodiments, the first temperature is about 1° C.

In some embodiments, the first controlled rate is between about 0.75° C. and 1.25° C. per minute.

In some embodiments, the second temperature is about −2° C.

In some embodiments, the second controlled rate is between about 20° C. and 30° C. per minute.

In some embodiments, the third temperature is about −60° C.

In some embodiments, the third controlled rate is between about 5° C. and 15° C. per minute.

In some embodiments, the fourth temperature is about −25° C.

In some embodiments, the fourth controlled rate is between 0.75° C. and 1.25° C. per minute.

In some embodiments, the firth temperature is about −40° C.

In some embodiments, the fifth controlled rate is between 7° C. and 15° C. per minute.

In some embodiments, final temperature is less than or equal to −80° C.

In some aspects, a method is provided comprising cryopreserving engineered immune cells suitable for cell therapy, the method comprising (1) providing a container comprising a sample comprising immune cells suspended in a cryopreservation medium, wherein sample volume is at least 5 percent less than the full capacity volume of the container, wherein the sample volume is at least 10 mL; and (2) stepwise freezing a population of engineered immune cells at a controlled rate to minimize impact of latent heat of fusion, where the stepwise freezing comprises cooling the cells at a rate of between 0.75° C. per minute to 30° C. per minute to a final temp of −80° C. or below, thereby cryopreserving the cells.

7

Figure 3:
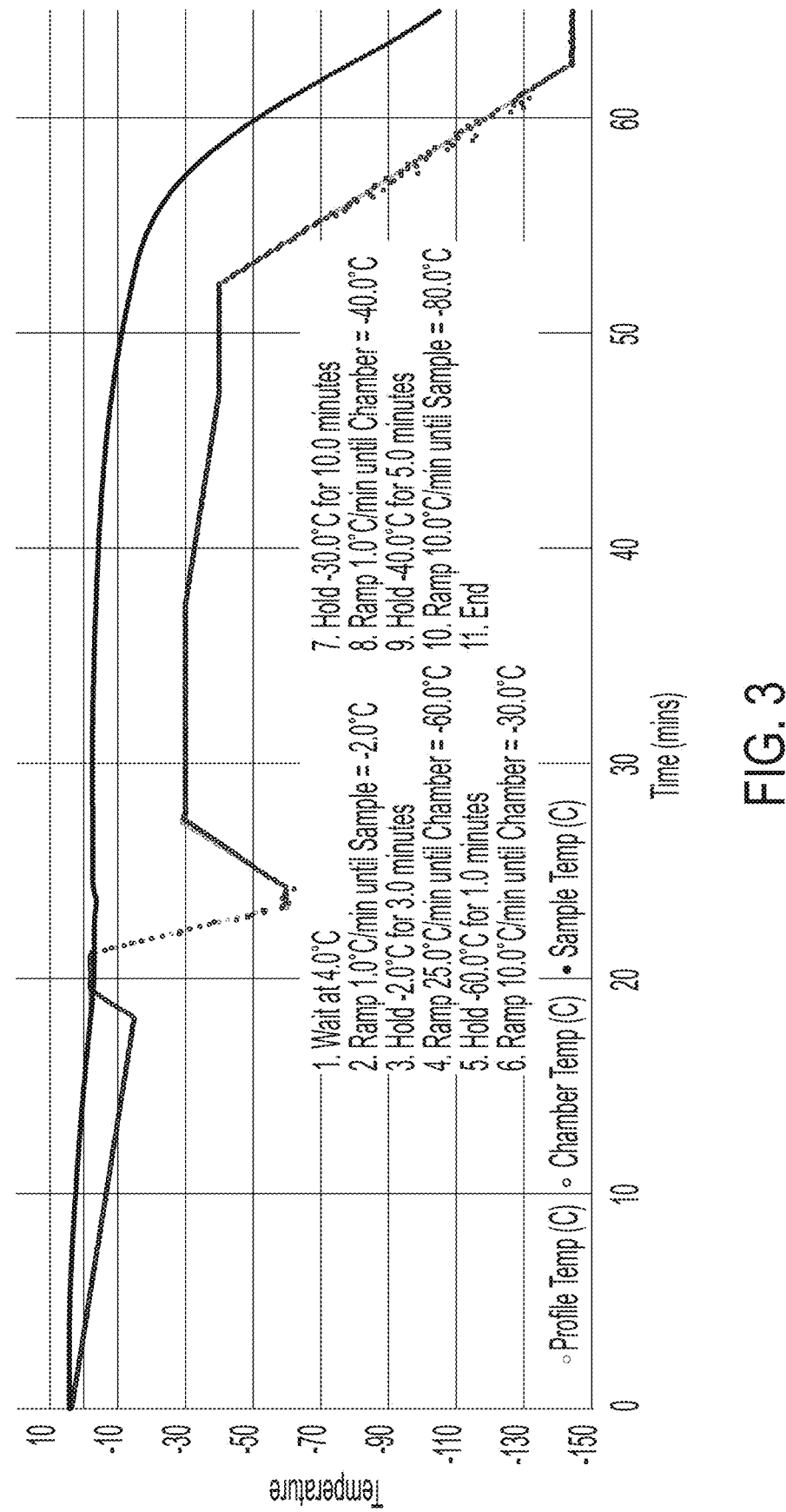

FIG. 3 is a graph showing the freeze profile of 36 ml of CAR-NK cells using a 60 minute freeze protocol as described herein, especially in Example 2. The CAR-NK cells were frozen in a controlled rate freezing device.

Figure 4:
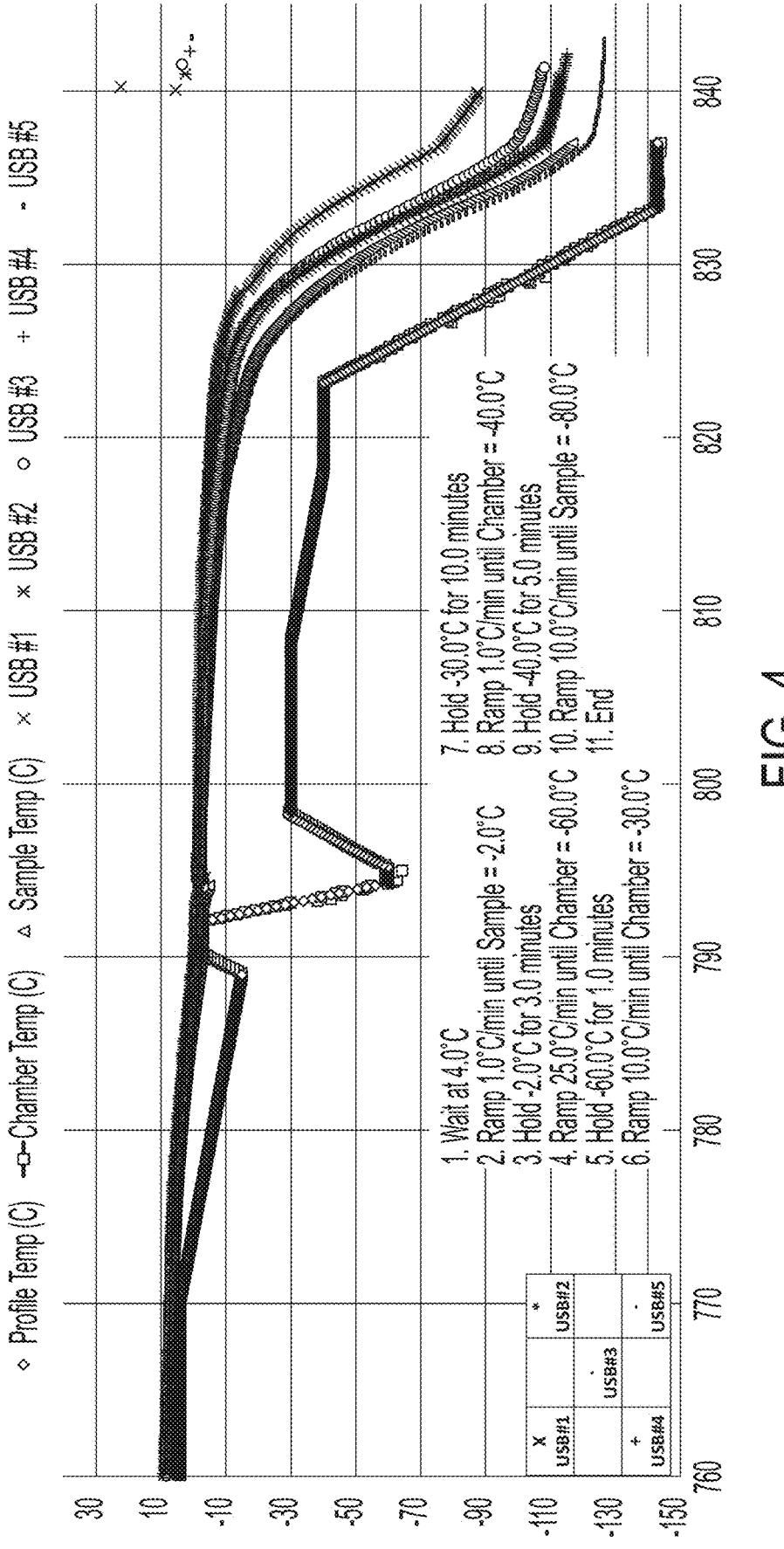

FIG. 4 is a graph showing the freeze profile of five 50 ml of AT vials, each comprising 16 mL, 30 mL and 45 mL of iCART cells (sometimes referred as iCART in this specification) The diagram in the left bottom corner shows the arrangement of 50 ml vials in the freezing device. USB designation refers to the placement of the vials in the freezing device.

Figure 5B:
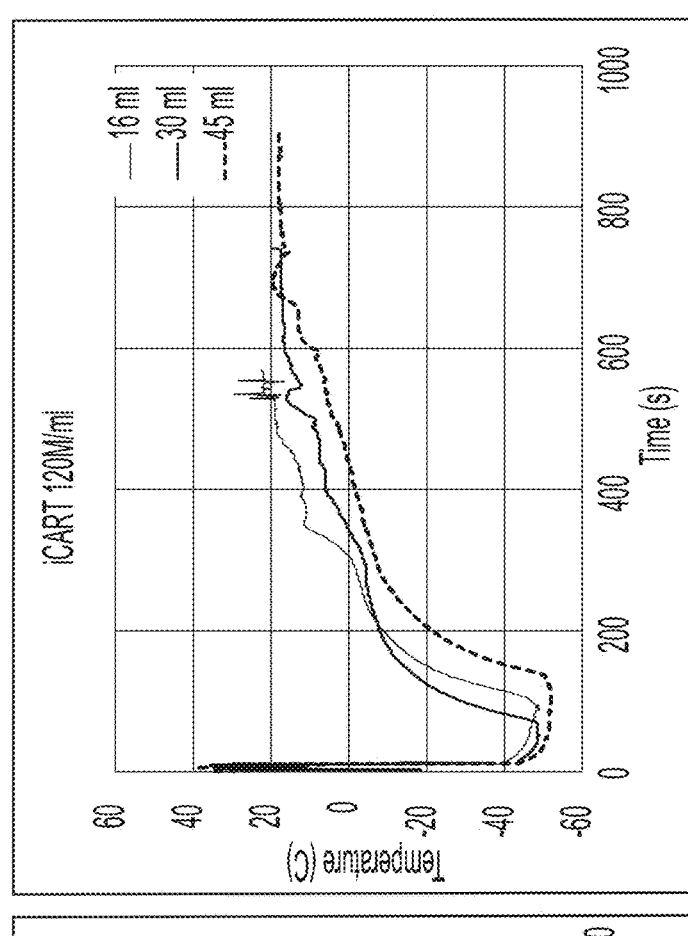
Figure 5A:
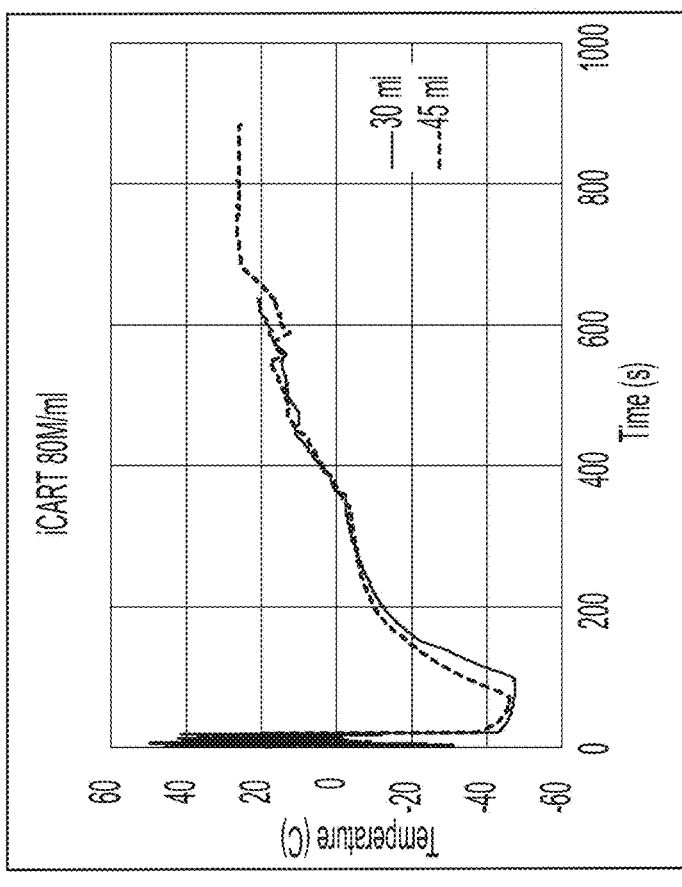

FIG. 5A is a graph showing thaw profile of 45 ml and 30 ml of frozen iCART at a concentration of 80 million cells per ml, in a 60° C. orbital shaker water bath, where the rotational speed of the orbital shaker is set at 150 rpm. FIG. 5B is a graph showing thaw profile of 45 ml, 30 ml and 16 ml of frozen iCART at a concentration of 120 million cells per ml, in a 60° C. orbital shaker water bath, where the rotational speed of the orbital shaker is set at 150 rpm.

Figure 6:
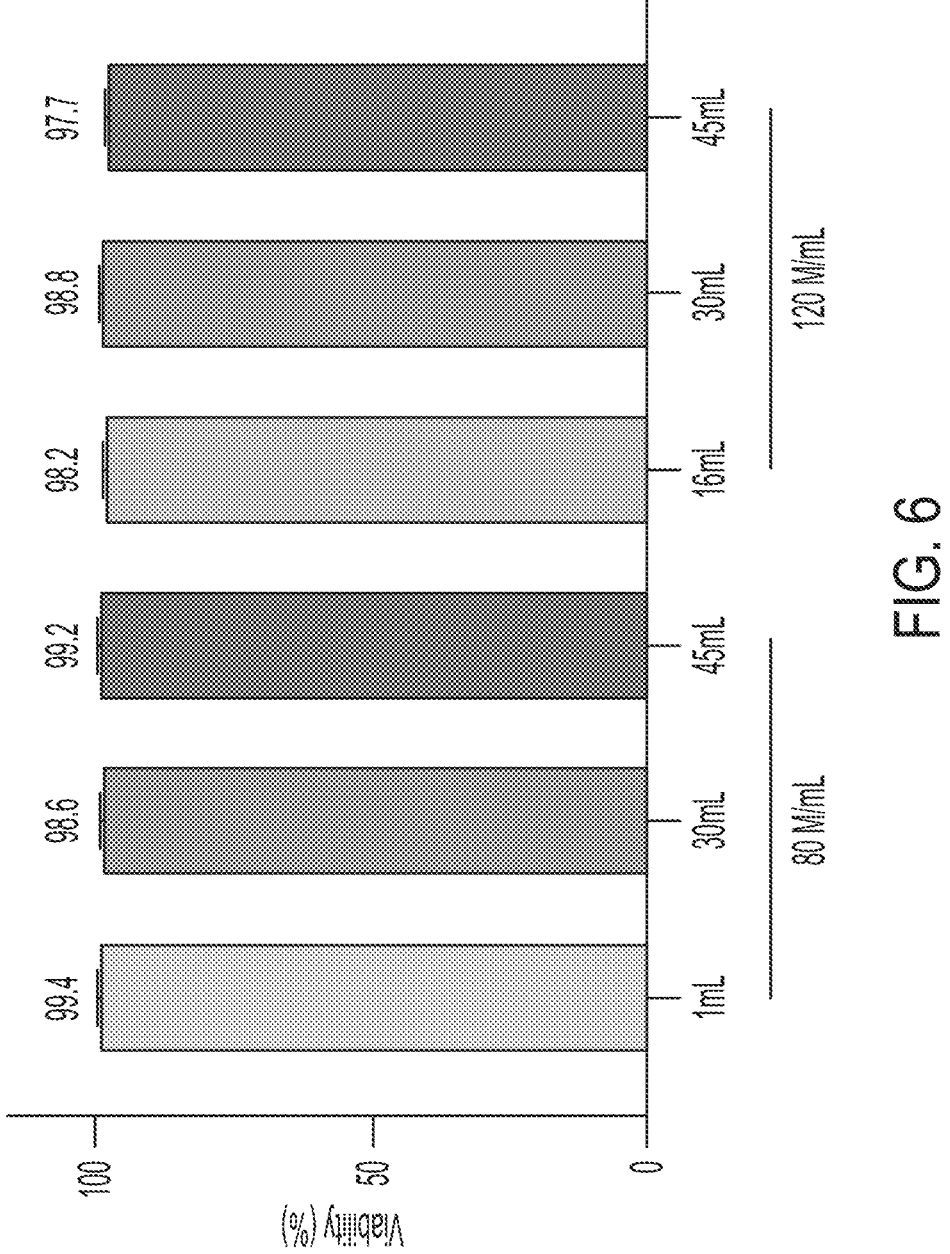

FIG. 6 is a graph showing the viability of iCART cells frozen using a freeze and thaw sequence described herein.

Figure 7A:
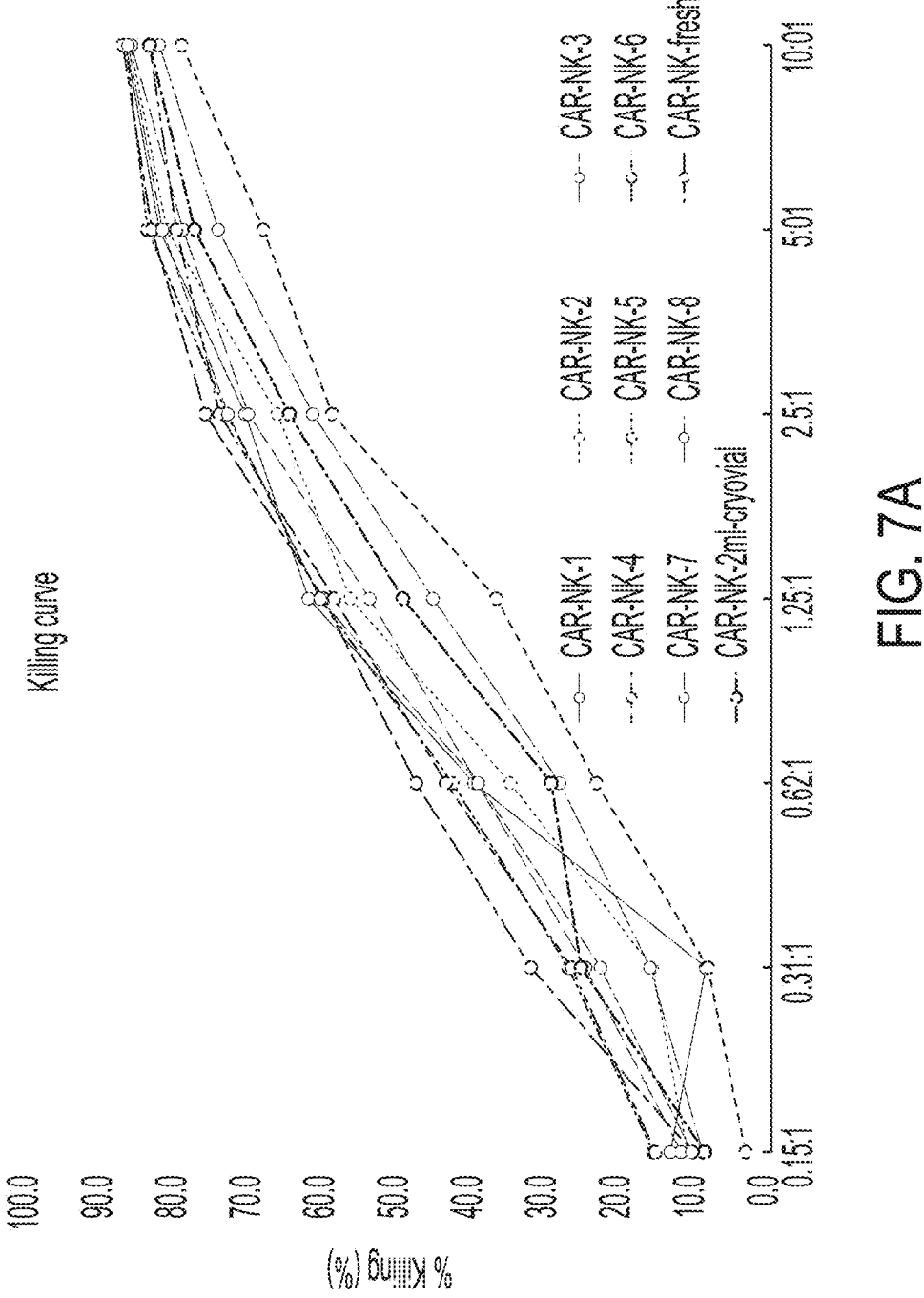

FIG. 7A depicts a graph showing comparable in vitro killing efficacy as a function of E:T (Effector:Target cells) ratio of frozen CAR-NK cells in 50 mL AT vials at different fill volume at both 80 million and 120 million per mL with freeze and thaw sequence described herein as compared to fresh cells, and with 2 mL cryovial and 2 mL AT vials. FIG. 7B is a table that depicts phenotypes of frozen, then thawed CAR-NK cells.

Figure 8A:
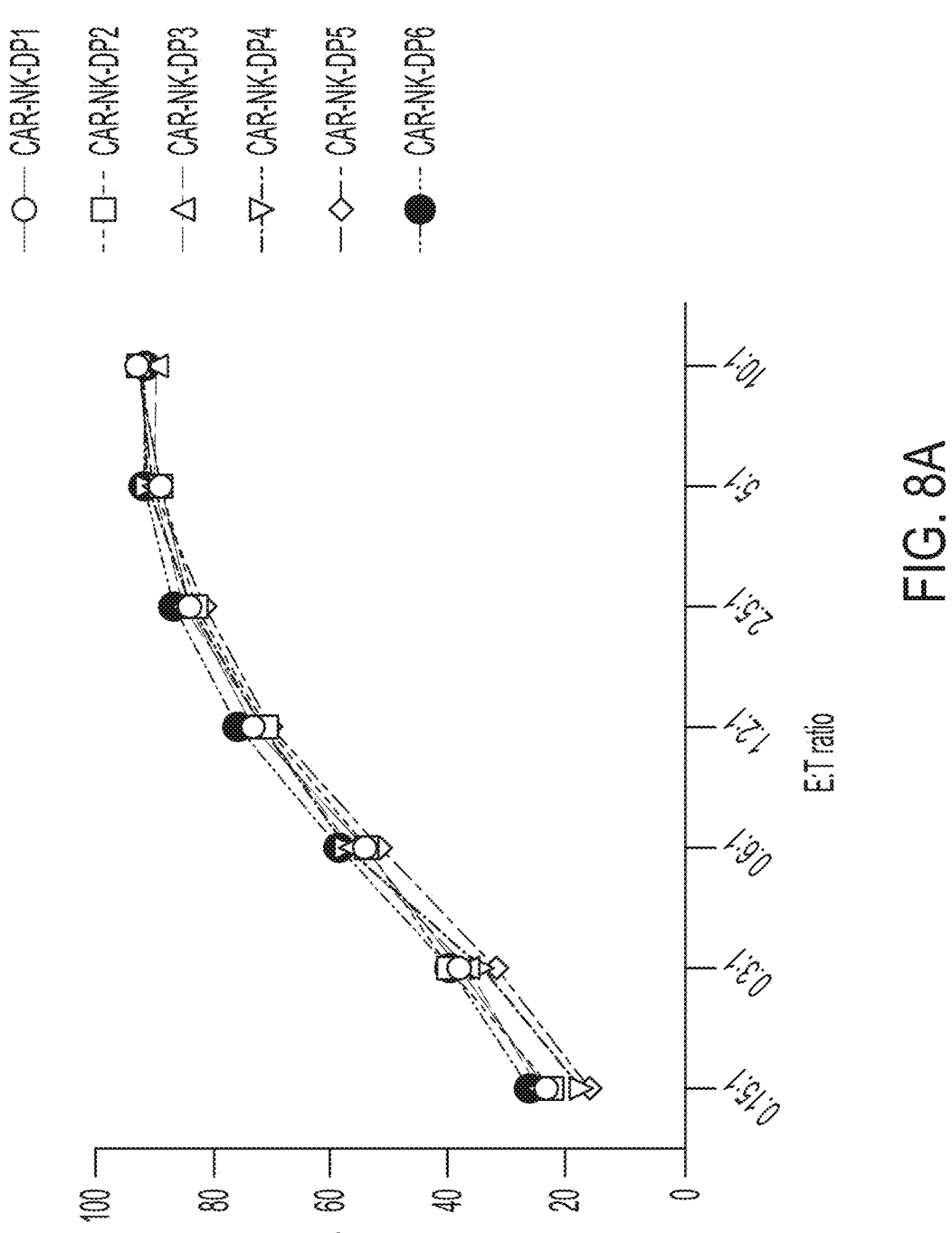

FIG. 8A depicts a series of graphs that show comparable in vitro killing efficacy as a function of E:T ratio of CAR-NK cells at 6 million and 80 million cells per mL with freeze and thaw sequence described herein as the frozen cells in 2 mL cryovials as reference cells. FIG. 8B and FIG. 8C are the data summary showing high (>96%) and comparable viability, killing efficacy and phenotyping of large volume of 50 mL vials as reference cells in 2 mL cryovials.

Figures 9A, 9B, 9C:
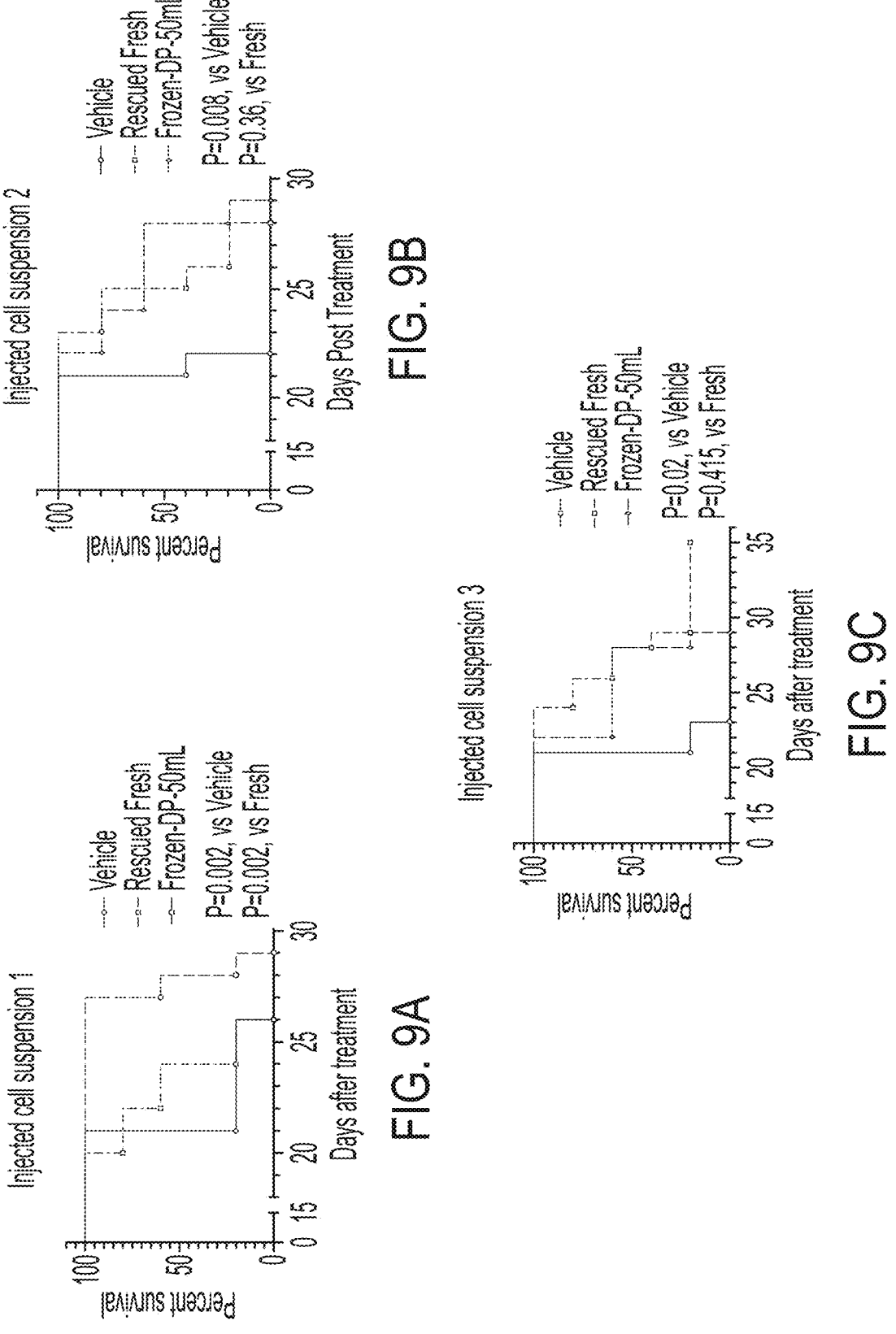

FIG. 9A-9C are a series of graphs that show the in vivo percent survival of tumor mouse models that were administered once-frozen and subsequently thawed CAR-NK cells. The graphs show tumor mouse model animal survival following administration of once-frozen and subsequently thawed CAR-NK cells (Cell suspensions #1-#3) in comparison to vehicle (freezing media without cells), and in comparison to cells that were rescued fresh CAR-NK cells. FIG. 9A shows the percent animal survival following administration of CAR-NK cells ("Cell Suspension #1).

FIG. 9B shows the percent animal survival following administration of CAR-NK cells into tumor mouse models. FIG. 9C shows the percent animal survival following administration of CAR-NK cells into tumor mouse model.

Figures 9D, 9E, 9F:
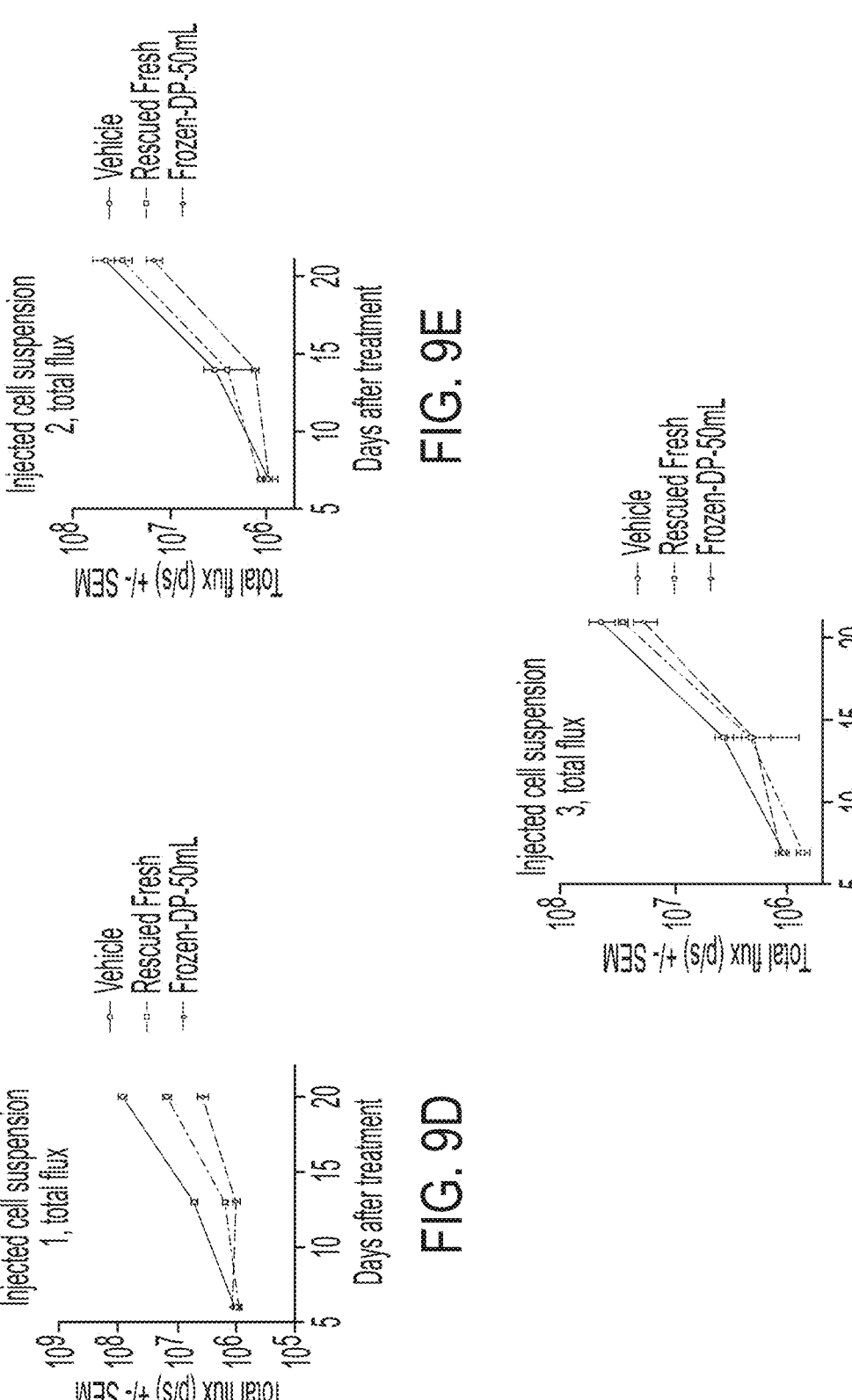

FIG. 9D-9F are a series of graphs that show in vivo total flux of luciferase fluorescence of tumor mouse models injected with once-frozen and subsequently thawed CAR-NK cells (cell suspensions #1-3) as compared to vehicle (freezing media without cells) and in comparison to rescued fresh CAR-NK cells.

Figure 9G:
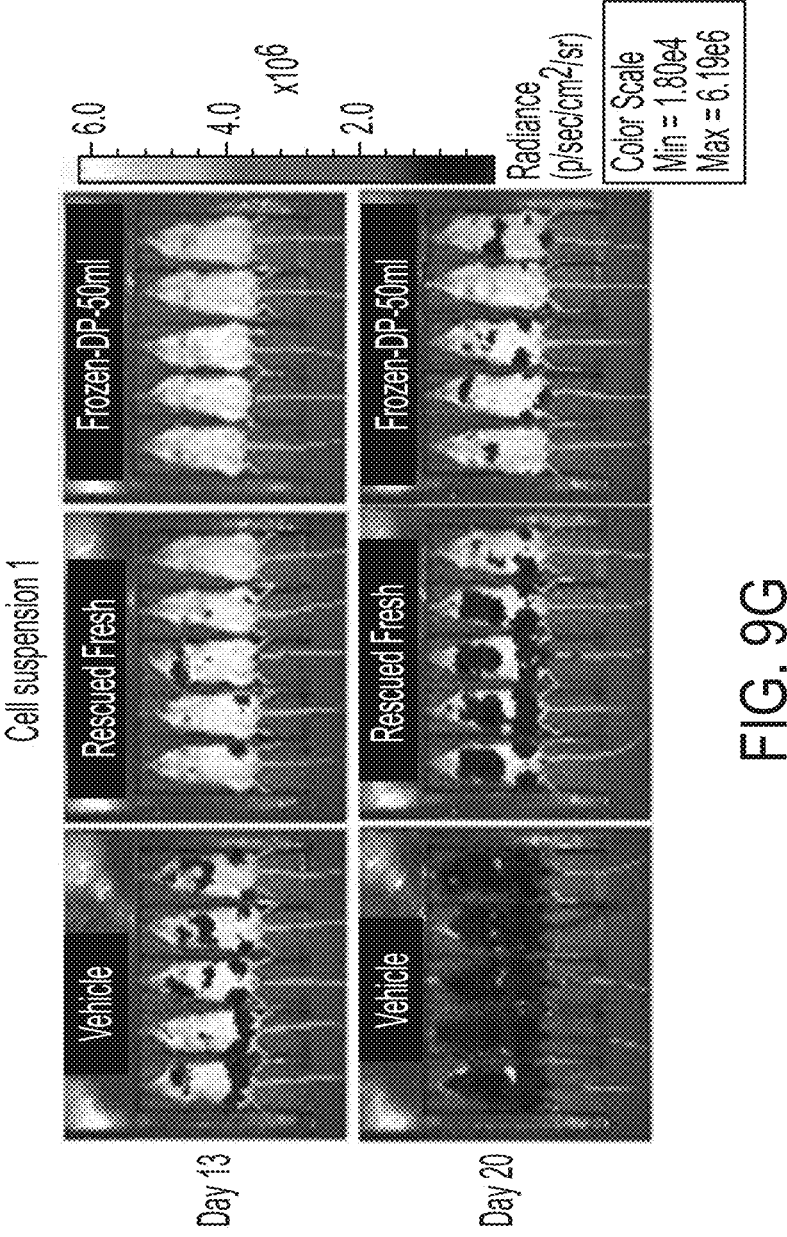
Figure 9H:
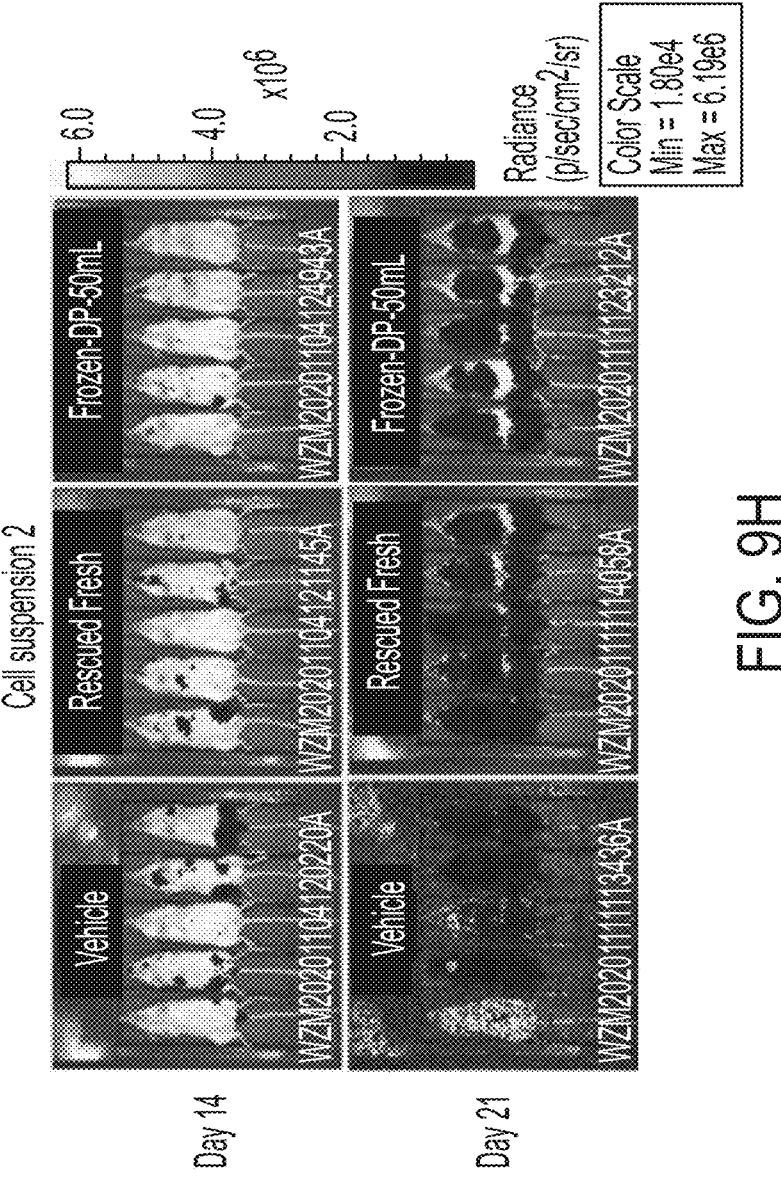
Figure 9I:
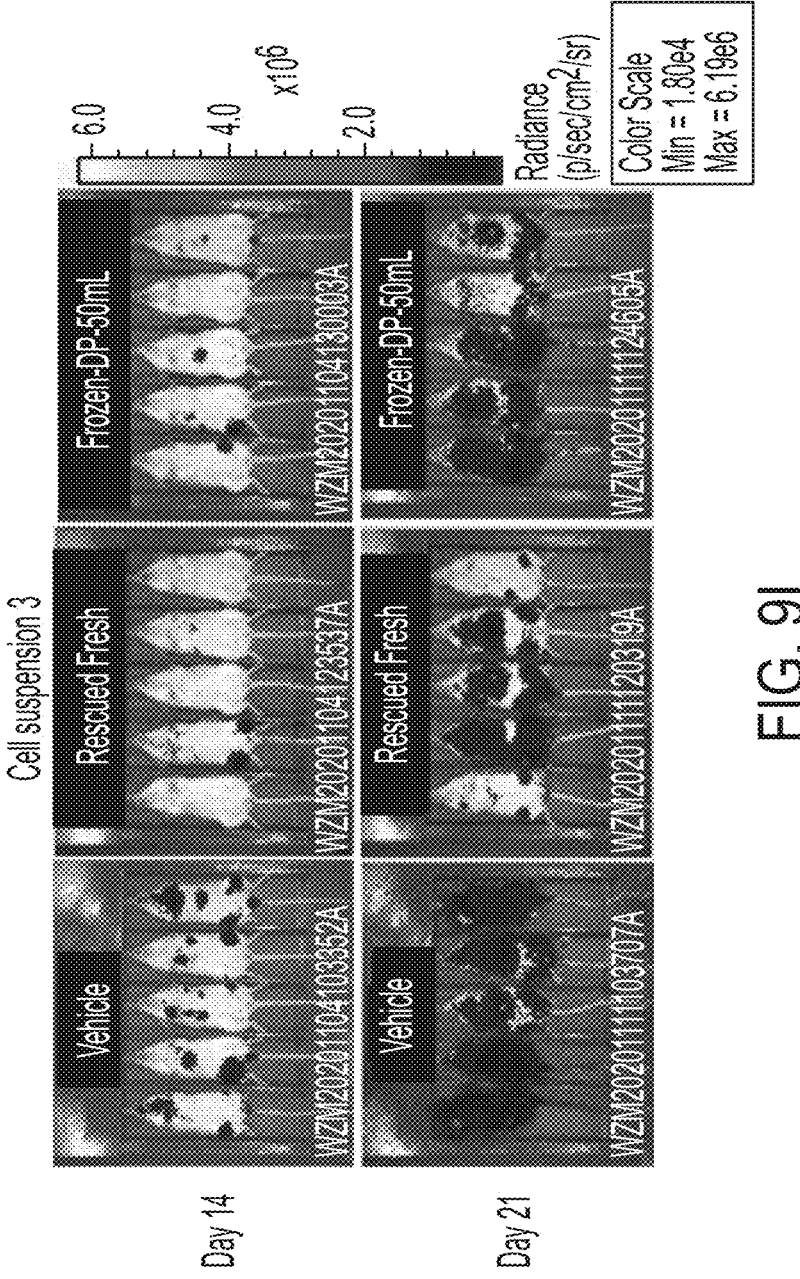

FIG. 9G-9I are a series of images that show luciferase activity in mice that were injected with once-frozen and subsequently thawed NK cells (cell suspensions #1-3), as compared to vehicle (freezing media without cells), and in comparison to rescued fresh CAR-NK cells.

DEFINITIONS

Allogeneic: As used herein, allogeneic refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically Approximately or about: As used herein, the term "approximately" or "about," as applied to one or more values of interest, refers to a stated value of interest as well as value that is similar to a stated reference value. In certain embodiments, the term "approximately" or "about" refers to a stated value of interest as well as range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biological sample: The term "biological sample" as used in this specification includes cells (both eukaryotic and prokaryotic), organs and tissue composed of cells, viruses, all of which can be natural or genetically or otherwise modified, and biologically active molecules such as macromolecules including cells, nucleic acids, protein, glycoproteins, lipids, lipoproteins, by way of example. The invention finds particular application in the cryoprotection of immune cells of human and other mammals.

Fresh cell or Rescued Fresh Cell: As used herein, the terms "fresh," "fresh cell," or "rescued fresh cell" refers to mammalian cells that have never been frozen and/or once frozen but subsequently restimulated, cultured in culture medium and then harvested as fresh cells.

Container: The term "container" as used herein shall be given its ordinary meaning and includes carriers, holders, enclosures, and conduits for containing, holding, administering, delivering, or transporting materials such as cryopreserved cells and associated compounds. Thus, in one embodiment, a container is unreactive with DMSO. In another embodiment, a container (e.g., an aseptic cryovial) used herein is both DEHP-free and DMSO resistant. Exemplary suitable containers include cryovials, cryobags and the like. Various kinds of cryovials are known, and include, for example, AT® cryovials, Nunc™ vials, glass vials and the like.

Controlled Cooling or Cooling at a Controlled Rate: The terms "controlled cooling" or "cooling at a controlled rate" and similar terms as used herein, is a process which applies an external cooling regime that results in a decrease in temperature of a biological sample cooled at a rate between for example, 0.1° C./minute and 50° C./minute. In some embodiments, the controlled cooling can be achieved using a commercially available freezer such as a controlled rate freezer. Various examples of controlled rate freezers and include, for example, but not limited to, CryoMed™ Model 5474, Strex CytoSensei SB02-0920, Custom BioGenic Systems Model 2101.

Cryoprotectant: As used herein, the term "cryoprotectant" refers to a substance used to protect biological tissue from freezing damage. Exemplary cryoprotectants include, for example, dimethyl sulfoxide (DMSO), glycerol, ethylene glycol and propanediol.

Cryopreservation: As used herein, the term "cryopreservation" or "freezing" generally refers to a method in which cells are frozen to maintain cellular viability. Cryopreserved cells maintain viability for an extended period of time in the frozen state, such as for 1, 5, 10 or more years in the cryopreserved state. The cryopreserved cells, once thawed, are able to propagate both for in vitro and in vivo applications.

Immune cells: The term "immune cells" as used herein denotes lymphocytes with helper, cytolytic or regulatory properties such as, for example, T cells, B cells, NK cells, macrophages, neutrophils, eosinophils, basophils, CD4+ T cells, CD8+ T cells, CD4+CD8+ T cells, CD4+CD8dim T cells, CD4+ regulatory T cells, CD56+CD8+ and CD56-CD57+CD8+ NKT, CAR-T-cells as well as CD16+CD56+ NK cells. However, the term "immune cells" as used herein does not mean only immune cells held and multiplied in vitro in culture media but also immune cell populations taken from a healthy blood donor, patient or an animal as well as respectively purified immune cells. In some embodiments, "immune cells" can be used to define T-cell modified by expressing a chimeric antigen receptor (CAR). In some embodiments, "immune cells" can be used to define NK-cell modified by expressing a CAR. In some embodiments, the "immune cells" are HSC cells. In some embodiments, the "immune cells" are MSC cells. In some embodiments, the "immune cells" are cord blood derived immune cells. In some embodiments, the "immune cells" are iPS cells derived immune cells. In some embodiments, the "immune cells" are T-regulatory cells. In some embodiments, the "immune cells" are gamma-delta T-cells. In some embodiments, NK cells comprise an anti-CD19 chimeric antigen receptor (CAR), IL-15, and inducible caspase-9-based suicide gene (iCaspase9). Thus in some embodiments, NK cell are engineered (e.g., using viral transduction or a non-viral method) to express a suicide gene, an anti-CD19 CAR gene and IL-15 gene.

In a particular embodiment, an exemplary CAR-NIK cell includes a CD19-CAR comprising an anti-CD19 binding domain comprising a light chain variable region comprising the amino acid sequence set forth in SEQ ID NO: 1 or a sequence having at least 95% identity thereto and/or a heavy chain variable region comprising the amino acid sequence set forth in SEQ ID NO: 2 or a sequence having at least 95% identity thereto. In some embodiments, the genetically engineered cord blood NK cells include a nucleic acid molecule encoding the heavy chain variable region of an anti-CD19 binding domain and/or a nucleic acid molecule encoding the light chain variable region of an anti-CD19 binding domain.

Latent Heat or Latent Heat of Fusion: The term "Latent Heat of Fusion" or "latent heat" as used in its broadest sense as indicative of any substance or phenomenon wherein, as heat is applied to the substance at a substantially uniform rate in the process of fusing the same, a point is reached where the temperature of the substance temporarily ceases to rise while heat is being absorbed for the modification of the molecular structure and internal energy of the substance. During freezing, release of the latent heat during phase change from liquid to solid state increases the temperature of the surroundings, leading to cessation of vitrification. In some embodiments, the latent heat of fusion can cause melting of ice. In some embodiments, the melting of ice causes the concentration of the sugars, salts, and cryoprotectant (e.g. DMSO or glycerol) to increase, and, consequently, also causes the osmotic pressure of the unfrozen fraction, to increase rapidly. In some embodiments, the increase in the osmotic strength causes an efflux of water from cells. In some embodiments, as cooling continues, these processes continue until the viscosity of the unfrozen fraction becomes too high for any further crystallization.

Minimize effects of Latent heat offusion: The term "minimize effects of latent heat of fusion" or "minimize impact of latent heat of fusion" refers to a process that involves formation of ice crystals or inducing ice nucleation outside of the cells in a biological sample. In some embodiments, the impact of latent heat of fusion is minimized by a continuous smooth temperature drop, by controlled cooling, to enable gradual extracellular ice formation while intracellular water moves out through osmosis. In some embodiments, ice nucleation supports the gradual growth of extracellular ice and limits supercooling. In some embodiments, increase in extracellular ice leads to dehydration of water from cells. In some embodiments, the quantity of ice crystals that formed depends on the initial composition of the solution. In some embodiments, cryoprotectants delay intracellular freezing by depressing freezing point. In some embodiments, cryoprotectants can penetrate the cell, in order to delay intracellular freezing.

Ice Nucleation: The term "ice nucleation" refers to a process that occurs in the formation of an ice crystal from a solution, and thermodynamically favors the formation of more ice crystals from water present in the solution. Nucleation is a stochastic process, occurring at particular sites on surfaces in the system. Nucleation can be induced by cooling temperatures or concentrating water up to conditions where the liquid or solution is significantly less thermodynamically stable than a crystal. Nucleation can further be induced by introduction of pre-existing ice crystals at a favorable temperature. In some embodiments, ice nucleation can be induced by introduction of ice crystals into a container using copper wires. In some embodiments, ice nucleation can be induced by lowering the temperature.

Orbital Shaker water bath: The term "orbital shaker water bath" as used herein refers to an water bath apparatus that reliably produces an orbital or cyclic motion at a set speed for a predetermined amount of time, comprising a movable tray for supporting articles which are to be agitated such as clinical assays in beakers, flasks, test tubes or the like.

Mammal: The term "Mammal" as used herein refers to any member of the class Mammalia, including, without limitation, humans and nonhuman primates such as chimpanzees, and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

Storage Temperature: The term "storage temperature", as used herein, refers to the temperature at which the cells are stored. In some embodiments, the cells are stored in liquid nitrogen vapor phase. In some embodiments, the cells are stored at a temperature below −60° C. In another embodiment, the cells are stored at a temperature ranging from −60° C. to −140° C. In another embodiment, the cells are stored at a temperature ranging from −60° C. to −196° C. In some embodiments, the cells are stored at or below a temperature of −140° C. In some embodiments, the cells are stored at temperature below −196° C.

Shipping Temperature: The term "shipping temperature" as used herein refers to the temperature at which the cells are shipped or transported, e.g., from a first location where the cells may be manufactured and/or cryopreserved to a second location where the cells may be thawed and subsequently administered to a subject in need thereof. In some embodiments, the cells are shipped in liquid nitrogen vapor phase. In some embodiments, the cells are shipped at a temperature of −140° C. or below −140° C. In some embodiments, the cells are stored and/or shipped at a temperature of −140° C. or below −140° C.

Vitrification: The term vitrification is defined as a process of rapid freezing a sample, preferably, a biological sample. In some embodiments, vitrification precludes formation of ice. In some embodiments, the process of vitrification requires the presence of cryoprotectants. In some embodiments, the process of vitrification requires a means of cooling the temperature rapidly.

The recitation of numerical ranges by endpoints herein includes all numbers and fractions subsumed within that range (e.g. 1 to 5 includes 1, 1.5, 2, 2.75, 3, 3.9, 4 and 5). It is also to be understood that all numbers and fractions thereof are presumed to be modified by the term "about."

Various aspects of the invention are described in detail in the following sections. The use of sections is not meant to limit the invention. Each section can apply to any aspect of the invention. In this application, the use of "or" means "and/or" unless stated otherwise. As used herein, the singular forms "a", "an", and "the" include both singular and plural referents unless the context clearly dictates otherwise.

Description

The process of cryoprotection can be lethal to the survival of cells. When the media around the cells are cooled at slow rates for preservation of cells, for example immune cells, cell-freezing rarely occurs at the freezing point of the medium. Samples may supercool to temperatures as low as −21° C. Excessive degrees of supercooling have a deleterious effect on the survival of some biological samples when they are left to continue cooling in the same vessel after ice formation.

Without wishing to be being bound to theory, the reason for this deleterious effect (low survival rate) is believed to be as follows. At ice formation, the latent heat of fusion causes the sample temperature to rise close to that of the melting point of the medium. Simultaneously, the temperature of the bath (or other surroundings) is continuing to fall at a constant rate; therefore, the greater the degree of supercooling, the larger the temperature difference that will exist between the cooling vessel and the sample immediately after ice formation. This, in turn, will increase the cooling rate of the sample above the normal optimal rate for survival of the sample (particularly in the case of an immune cells), until thermal equilibrium is reestablished with the surroundings.

The challenge to cells during the cryopreservation is not their ability to endure storage at very low temperatures (below −120° C.); rather, it is the lethality of the cooling-freezing and the warming-thawing processes. As cells are cooled to approximately −5° C., both the cells and surrounding medium remain unfrozen and supercooled. Between −5° C. and approximately −15° C., ice forms (either spontaneously or as a result of artificially introducing ice crystals, i.e. seeding, to the solution) in the external medium; however, the cells' contents remain unfrozen and supercooled, presumably because the plasma membrane blocks the growth of ice crystals into the cytoplasm. The supercooled water in the cells has, by definition, a greater chemical potential than that of water in the partially frozen extracellular solution; and water thus flows out of the cells osmotically and freezes externally.

The subsequent physical events in the cells depend on the cooling rate. If cells are cooled too rapidly, intracellular water is not moving out of cells fast enough to extracellular space to maintain equilibrium; the cells become increasingly supercooled, leading to intracellular ice formation (IIF) which kill the cells. However, if the cells are cooled too slowly, they will experience a severe dehydration with volume shrinkage and long-term exposure to high-solute concentrations (composed mainly of electrolytes) before they reach a eutectic temperature (when all components in a solution are solidified). Both the cell shrinkage and the long-time exposure to high-electrolytes concentrations can cause cell injury (so-called "osmotic injury"). As a result, the cells dehydrate and do not freeze intracellularly. Therefore, cooling rate that is either too high or too low can damage cells, although the mechanisms underlying cell damage are different.

Only when cooling is controlled at an optimal rate to enable cells to lose water rapidly enough to concentrate the intracellular solutes sufficiently to eliminate supercooling while preventing cells from severe dehydration, the cells functionality is preserved. The optimal cooling rate for cell functionality preservation should be slow enough to avoid IIF but fast enough to minimize the severe cell dehydration.

Besides, if a cell has survived cooling-freezing to low temperatures, it is still facing a great challenge during the warming-thawing process, due to the lethal ice-recrystallization (LIR), i.e. the growth of small intracellular ice crystals into harmful large ice crystals during the warming-thawing process. An optimal rapid warming rate or programs coupled with the cooling rate/program is absolutely required to prevent LIR for the cell cryo-survival.

A controlled cooling rate and rapid warming rate for a small sample (<5 mL) is easy to achieve in research labs. However, the modern industrial manufacturing of large-scale therapeutic cells is facing a big existing problem, namely, how to achieve and control the cell optimal cooling and rapid warming rates for cryopreservation of a large volume sample (>25 mL), which is becoming a critical technical bottleneck for cryopreservation and commercialization of therapeutic cell products in mass production, and their shipping as well as clinical practice.

This methods disclosed herein include (1) a coupled optimal cooling (with a specific ice nucleation seeding program to prevent supercooling) and rapid warming rate conditions and programs, for cryopreservation of mammalian cells, including immune cells (e.g., natural immune cells and developed CAR-T and CAR-NK cells); (2) methods and programs to achieve the above optimal cooling rates for large vialed samples (e.g., large volume cell suspensions in 10 mL or greater containers), using a liquid nitrogen controlled freezer; and (3) methods and programs to achieve the above optimal rapid warming rates for large vialed samples (e.g. large volume cell suspensions in 50 mL AT closed vials), using an orbital-shaker water bath at temperatures above 50° C. for cell suspension ranging fill volume of 8 to 45 mL in vials and cell concentration of 6-120 million cells per mL. In some embodiments, the cell concentration is between about 6-25 million cells per mL.

Methods of Cryopreservation

In general, it is known that when liquid water is cooled it undergoes a phase transition from liquid to solid at a critical temperature. The phase transition is a first-order transition, which means the water either absorbs or releases an amount of energy per volume known as the latent heat. During the phase transition the temperature of the water will remain constant as heat is added or removed and during this time the water is in a mixed-state, where some of it is in a liquid state and some is in a solid state. The temperature at which a phase transition happens can be called the critical temperature of the phase transition. When water is cooled the temperature of the water decreases until the critical temperature is reached. While cooling is still applied the temperature of the water remains constant until the latent heat has been removed from the water after which the temperature of the water, now in solid state, once again decreases. This means that there is a duration of time during which latent heat is being removed from the water. The time during which latent heat is removed in the process of freezing is the time when ice crystals may form, which is undesirable when cryopreserving samples containing biological materials such as cells.

The cryopreservation media described herein used with the cryopreservation methods described herein minimize the impact of latent heat during cryopreservation (i.e., ice formation impact), thereby resulting in a higher viability of cell sample, which has been frozen.

Methods of cryopreservation described herein are performed on cell suspensions of mammalian immune cells. In some embodiments, the stepwise cryogenic freezing sequence is scalable to up to 30 vials or more, each vial having a cell sample volume of 10-40 mL or more. In some embodiments, the freezing sequence is scalable to 30 vials, 50 vials, or 75 vials. In some embodiments, current methods of cryopreservation are performed on mammalian immune cell suspensions in cryovials, cryobags, AT® vials or Nunc™ vials or Glass vials. In some embodiments, current methods of cryopreservation are performed on mammalian immune cell suspensions in cryovials or AT® vials or any other suitable container. In some embodiments, suitable containers are those that are unreactive with DMSO. In some embodiments, the cryovials, cryobags, AT® vials or Nunc™ vials, glass vials and other containers used for cryopreservation, are compatible for use with DMSO. In some embodiments, the cryovials, cryobags, AT® vials or Nunc™ vials, glass vials and other containers used for cryopreservation, are both DEHP-free as well as DMSO resistant.

Various containers can be used in the methods of cryopreservation including, for example, cryovials or cryobags. Exemplary cryovials, include, for example, AT® vials or Nunc™ vials or glass vials. In some embodiments, current methods of cryopreservation are performed on mammalian immune cell suspensions in cryovials or AT® vials or any other suitable container. In some embodiments, suitable containers are those that are resistant to DMSO. In some embodiments, the cryovials, cryobags, AT® vials or Nunc™ vials, glass vials and other containers used for cryopreservation, are compatible for use with DMSO. In some embodiments, the cryovials, cryobags, AT® vials or Nunc™ vials, glass vials and other containers used for cryopreservation, are chemically unreactive with DMSO. In some embodiments, the containers used for cryopreservation are both DEHP-free and DMSO-resistant (e.g., AT® vials). In various embodiments, the containers used herein (e.g., AT® vials) facilitate aseptic transfer of cells directly into a subject in need thereof via a vial adapter.

Containers used herein can have various dimensions, including those dimensions discussed herein. In some embodiments, the dimensions suitable for use with cryovials as discussed herein are also suitable for use with other containers, such as AT® vials or Nunc™ vials.

In some embodiments, the freeze/thaw methods described herein allow for the consistent freezing and thawing of a cell containing sample at a large scale, such as for example 10 mL in volume or more. In some embodiments, the freeze/thaw methods described herein can be used with a sample having a volume of 10 mL or more. In some embodiments, the freeze/thaw methods described herein can be used with a sample having a diameter of greater than 225 mm/inch. In some embodiments, the freeze/thaw methods described herein can be used with a sample having a solution height of greater than 225 mm/inch. In some embodiments, the freeze/thaw methods described herein can be used with a sample having a solution thickness of greater than 225 mm/inch.

In some embodiments, the cryovials have a dimension between about 5 mm external diameter and 100 mm height. In some embodiments, the cryovials have a dimension of about 10 mm external diameter and 75 mm height. In some embodiments, the cryovials have a dimension, of 10 mm external diameter and 50 mm height.

In some embodiments, the cryovials have a dimension of 10 mm external diameter and 48.3 mm height. In some embodiments, the cryovials have a dimension of 10.5 mm external diameter and 48.3 mm height. In some embodiments, the cryovials have a dimension of 11.0 mm external diameter and 48.3 mm height. In some embodiments, the cryovials have a dimension of between 11.5 mm external diameter and 48.3 mm height. In some embodiments, the cryovials have a dimension of 12.0 mm external diameter and 48.3 mm height. In some embodiments, the cryovials have a dimension of 12.5 mm external diameter and 48.3 mm height. In some embodiments, the cryovials have a dimension of 13.0 mm external diameter and 48.3 mm height. In some embodiments, the cryovials have a dimension of 13.5 mm external diameter and 48.3 mm height. In some embodiments, the cryovials have a dimension of 14.0 mm external diameter and 48.3 mm height. In some embodiments, the cryovials have an external of 14.5 mm external diameter and 48.3 mm height. In some embodiments, the cryovials have a dimension of 15.0 mm external diameter and 48.3 mm height.

In some embodiments, the cryovial has a height of between about 30 mm to about 85 mm. In some embodiments, the cryovial has an external diameter of about between 15 mm to about 40 mm. In some embodiments, the cryovial has a maximum volume capacity of between about 1 mL and 55 mL. Various kinds of cryovials are suitable for the compositions and methods described herein. Exemplary cryovials, including description of cryovial dimensions can be found at http://www.aseptictech.com/sites/default/files/brochure_vialslines_v3.0.pdf the contents of which are incorporated herein by reference in its entirety.

In some embodiments, the cryovials have a height of between about 45 mm and 100 mm. In some embodiments, the cryovials have a height of 45.3 mm. In some embodiments, the cryovials have a height of 45.6 mm. In some embodiments, the cryovials have a height of 46 mm. In some embodiments, the cryovials have a height of 46.3 mm. In some embodiments, the cryovials have a height of 46.6 mm. In some embodiments, the cryovials have a height of 47 mm. In some embodiments, the cryovials have a height of 47.3 mm. In some embodiments, the cryovials have a height of 47.6 mm. In some embodiments, the cryovials have a height of 48 mm. In some embodiments, the cryovials have a height of 48.3 mm. In some embodiments, the cryovials have a height of 48.6 mm. In some embodiments, the cryovials have a height of 49 mm. In some embodiments, the cryovials have a height of 49.3 mm. In some embodiments, the cryovials have a height of 50 mm. In some embodiments, the cryovials have a height of 50 mm., In some embodiments, the cryovials have a height of 50 mm. In some embodiments, the cryovials have a height of 55 mm. In some embodiments, the cryovials have a height of 60 mm. In some embodiments, the cryovials have a height of 55 mm. In some embodiments, the cryovials have a height of 65 mm. In some embodiments, the cryovials have a height of 55 mm. In some embodiments, the cryovials have a height of 70 mm. In some embodiments, the cryovials have a height of 75 mm. In some embodiments, the cryovials have a height of 80 mm. In some embodiments, the cryovials have a height of 85 mm. In some embodiments, the cryovials have a height of 90 mm. In some embodiments, the cryovials have a height of 95 mm. In some embodiments, the cryovials have a height of 100 mm.

In some embodiments, the cryovials have an external diameter of 10 mm. In some embodiments, the cryovials have an external diameter of 10.5 mm. In some embodiments, the cryovials have an external diameter of 11 mm. In some embodiments, the cryovials have an external diameter of 11.5 mm. In some embodiments, the cryovials have an external diameter of 12 mm. In some embodiments, the cryovials have an external diameter of 12.5 mm. In some embodiments, the cryovials have an external diameter of 13 mm. In some embodiments, the cryovials have an external diameter of 13.5 mm. In some embodiments, the cryovials have an external diameter of 14 mm. In some embodiments, the cryovials have an external diameter of 14.5 mm. In some embodiments, the cryovials have an external diameter of 15 mm.

In some embodiments, the cryobags have a width of 11 cm. In some embodiments, the cryobags have a width of 11.3 cm. In some embodiments, the cryobags have a width of 11.5 cm. In some embodiments, the cryobags have a width of 11.7 cm. In some embodiments, the cryobags have a width of 11.9 cm. In some embodiments, the cryobags have a width of 12.1 cm. In some embodiments, the cryobags have a width of 12.3 cm. In some embodiments, the cryobags have a width of 12.5 cm. In some embodiments, the cryobags have a width of 12.7 cm. In some embodiments, the cryobags have a width of 12.9 cm. In some embodiments, the cryobags have a width of 13.1 cm. In some embodiments, the cryobags have a width of 13.3 cm. In some embodiments, the cryobags have a width of 13.5 cm. In some embodiments, the cryobags have a width of 13.7 cm.

In some embodiments, the cryobags have a length of 14.1 cm. In some embodiments, the cryobags have a length of 14.3 cm. In some embodiments, the cryobags have a length of 14.5 cm. In some embodiments, the cryobags have a length of 14.7 cm. In some embodiments, the cryobags have a length of 14.9 cm. In some embodiments, the cryobags have a length of 15.1 cm. In some embodiments, the cryobags have a length of 15.3 cm. In some embodiments, the cryobags have a length of 15.5 cm. In some embodiments, the cryobags have a length of 15.7 cm. In some embodiments, the cryobags have a length of 15.9 cm. In some embodiments, the cryobags have a length of 16.1 cm. In some embodiments, the cryobags have a length of 16.3 cm. In some embodiments, the cryobags have a length of 16.5 cm. In some embodiments, the cryobags have a length of 16.7 cm.

In some embodiments the volume of the cryovials (i.e., maximum capacity) can be between 2 ml to 50 ml for example, 2 ml, 3 ml, 4 ml, 5 ml, 6 ml, 7 ml, 8 ml, 9 ml, 10 ml, 11 ml, 12 ml, 13 ml, 14 ml, 15 ml, 16 ml, 17 ml, 18 ml, 19 ml, 20 ml, 21 ml, 22 ml, 23 ml, 24 ml, 25 ml, 26 ml, 27 ml, 28 ml, 29 ml, 30 ml, 31 ml, 32 ml, 33 ml, 34 ml, 35 ml, 36 ml, 37 ml, 38 ml, 39 ml, 40 ml, 41 ml, 42 ml, 43 ml, 44 ml, 45 ml, 46 ml, 47 ml, 48 ml, 49 ml, 50 ml, 51 ml, 52 ml, 53 ml, 54 ml, 55 ml, 56 ml, 57 ml, 58 ml, 59 ml, 60 ml, 61 ml, 62 ml, 63 ml, 64 ml, 65 ml, 66 ml, 67 ml, 68 ml, 69 ml, 70 ml, 71 ml, 72 ml, 73 ml, 74 ml, 75 ml, 76 ml, 77 ml, 78 ml, 79 ml, 80 ml, 81 ml, 82 ml, 83 ml, 84 ml, 85 ml, 86 ml, 87 ml, 88 ml, 89 ml, 90 ml, 91 ml, 92 ml, 93 ml, 94 ml, 95 ml, 96 ml, 97 ml, 98 ml, 99 ml, or 100 ml.

As used herein, "fill volume" refers to the volume of the sample comprising cells in a container. In some embodiments, the fill volume is less than the maximum capacity of the container. In some embodiments, the fill volume in vials can be between 15% to 90% maximum capacity of the vial. For example, the fill volume in vials can be 15% maximum capacity, 20% maximum capacity, 25% maximum capacity, 30% maximum capacity, 35% maximum capacity, 40% maximum capacity, 45% maximum capacity, 50% maximum capacity, 55% maximum capacity, 60% maximum capacity, 65% maximum capacity, 70% maximum capacity, 75% maximum capacity, 80% maximum capacity, 85% maximum capacity or 90% maximum capacity. In some embodiments, a 2 ml cryovial has a fill volume of 1 ml. In some embodiments, a 50 ml cryovial has a fill volume of 8 ml to 45 ml. In some embodiments, a 50 ml cryovial has a fill volume of 8 ml. In some embodiments, a 50 ml cryovial has a fill volume of 10 ml. In some embodiments, a 50 ml cryovial has a fill volume of 12 ml. In some embodiments, a 50 ml cryovial has a fill volume of 14 ml. In some embodiments, a 50 ml cryovial has a fill volume of 16 ml. In some embodiments, a 50 ml cryovial has a fill volume of 18 ml. In some embodiments, a 50 ml cryovial has a fill volume of 20 ml. In some embodiments, a 50 ml cryovial has a fill volume of 22 ml. In some embodiments, a 50 ml cryovial has a fill volume of 24 ml. In some embodiments, a 50 ml cryovial has a fill volume of 26 ml. In some embodiments, a 50 ml cryovial has a fill volume of 28 ml. In some embodiments, a 50 ml cryovial has a fill volume of 30 ml. In some embodiments, a 50 ml cryovial has a fill volume of 32 ml. In some embodiments, a 50 ml cryovial has a fill volume of 34 ml. In some embodiments, a 50 ml cryovial has a fill volume of 36 ml. In some embodiments, a 50 ml cryovial has a fill volume of 38 ml. In some embodiments, a 50 ml AT vial has a fill volume of 40 ml. In some embodiments, a 50 ml cryovial has a fill volume of 42 ml. In some embodiments, a 50 ml cryovial has a fill volume of 44 ml. In some embodiments, a 50 ml cryovial has a fill volume of 45 ml. In some embodiments, the cryogenic container can have a volume of about 50 mL, about 75 mL, about 100 mL, about 250 mL, about 500 mL, about 750 mL, about 1 L, or more than about 1 L.

In some embodiments, the mammalian immune cells can be cryopreserved at a concentration between about 6 M/ml to about 120 M/ml. For example, in some embodiments, immune cells can be cryopreserved at a concentration of 6 M/ml. In some embodiments, immune cells can be cryopreserved at a concentration of 10 M/ml. In some embodiments, immune cells can be cryopreserved at a concentration of 15 M/ml. In some embodiments, immune cells can be cryopreserved at a concentration of 20 M/ml. In some embodiments, immune cells can be cryopreserved at a concentration of 25 M/ml. In some embodiments, immune cells can be cryopreserved at a concentration of 30 M/ml. In some embodiments, immune cells can be cryopreserved at a concentration of 35 M/ml. In some embodiments, immune cells can be cryopreserved at a concentration of 40 M/ml. In some embodiments, immune cells can be cryopreserved at a concentration of 45 M/ml. In some embodiments, immune cells can be cryopreserved at a concentration of 50 M/ml. In some embodiments, immune cells can be cryopreserved at a concentration of 55 M/ml. In some embodiments, immune cells can be cryopreserved at a concentration of 60 M/ml. In some embodiments, immune cells can be cryopreserved at a concentration of 65 M/ml. In some embodiments, immune cells can be cryopreserved at a concentration of 70 M/ml. In some embodiments, immune cells can be cryopreserved at a concentration of 75 M/ml. In some embodiments, immune cells can be cryopreserved at a concentration of 80 M/ml. In some embodiments, immune cells can be cryopreserved at a concentration of 85 M/ml. In some embodiments, immune cells can be cryopreserved at a concentration of 90 M/ml. In some embodiments, immune cells can be cryopreserved at a concentration of 100 M/ml. In some embodiments, immune cells can be cryopreserved at a concentration of 105 M/ml. In some embodiments, immune cells can be cryopreserved at a concentration of 110 M/ml. In some embodiments, immune cells can be cryopreserved at a concentration of 115 M/ml. In some embodiments, immune cells can be cryopreserved at a concentration of 120 M/ml.

In some embodiments, the CAR NK cells are provided in a dosage of about between $1\times10^6$ to $1\times10^7$ cells in a volume of about 36 mL in a 50 mL cryovial. In some embodiments, the CAR NK cells are provided in a dosage of about between $200\times10^6$ and $800\times10^6$ cells in a 50 mL cryovial. In some embodiments, the CAR NK cells are suspended in a cryopreservation medium as described herein, followed by cryopreservation as disclosed herein. Such cryopreserved NK cells can then be stored as described herein. The sample comprising NK cryopreserved NK cells are then thawed as described herein. The thawed cells are subsequently administered to a patient in need thereof. In some embodiments, a volume of about 33 mL, 34 mL, 35 mL, or 36 mL of the thawed cells are administered to a patient in need thereof using a vial adapter for aseptic administration. In some embodiments, a volume of about 33 mL of the thawed cells are administered to a patient in need thereof using a vial adapter for aseptic administration. In some embodiments, a volume of about 34 mL of the thawed cells are administered to a patient in need thereof using a vial adapter for aseptic administration. In some embodiments, a volume of about 35 mL of the thawed cells are administered to a patient in need thereof using a vial adapter for aseptic administration. In some embodiments, a volume of about 36 mL of the thawed cells are administered to a patient in need thereof using a vial adapter for aseptic administration.

In some aspects, a suitable medium for cryopreserving (i.e., a cryopreservation medium) cells comprises: a cryoprotectant, an albumin, a disaccharide and a non-pyrogenic and isotonic crystalloid solution. In various embodiments, cells once cryopreserved in a media described, can be thawed and subsequently administered to a patient, without the need to reformulate or resuspend the cells in another media or solution.

In several embodiments, mammalian immune cells are cryopreserved in a medium containing one or more cryoprotectants. Various cryoprotectants are known in the art and include, for example, dimethyl sulfoxide (DMSO), glycerol, and propanediol among others. In some embodiments, the cryopreservation medium comprises DMSO as a cryoprotectant.

In some embodiments, the cryopreservation of mammalian immune cells involve up to 9-step cryogenic freezing sequence. In some embodiments the step-wise freezing reduces latent heat of fusion of the biological sample being frozen. In some embodiments, cells are cooled in a temperature ramp-down phase having a selected rate of temperature reduction. In some embodiments, a rate of temperature reduction in a temperature ramp-down phase is about 10° C. per minute. In several embodiments, other rates of change are used, such as about 1° C. per minute, about 2° C. per minute, about 5° C. per minute, about 7° C. per minute, about 12° C. per minute, about 15° C. per minute, about 17° C. per minute, about 20° C. per minute, about 25° C. per minute, or rates within the values above. In several embodiments, a temperature ramp-down phase may include a flash freezing (e.g., maximal temperature reduction) step. For example, a flash freeze step may comprise a flash-freeze rate of temperature change having an increased rate of temperature reduction, where the rate is selected to advantageously improve cell integrity or cell viability. In contrast, in several embodiments and counter to conventional wisdom, a flash freeze step is not employed. Applicants have discovered, in certain embodiments, that maximal rates of temperature reduction are similarly damaging as certain slower rates of reduction, while certain intermediate rates provide an unexpectedly improved quality of cryopreservation and/or cell viability. In some embodiments, a temperature ramp-down phase may include cooling the substrate-adhered cells at a rate of approximately 10° C. per 10 seconds, 10° C. per 20 seconds, 10° C. per 30 seconds, 10° C. per 40 seconds, 10° C. per 50 seconds, 10° C. per 60 seconds, 10° C. per 70 seconds, 10° C. per 80 seconds, 10° C. per 90 seconds, 10° C. per 100 seconds, 10° C. per 110 seconds, 10° C. per 120 seconds, 10° C. per 130 seconds, 10° C. per 140 seconds, 10° C. per 150 seconds, 10° C. per 160 seconds, 10° C. per 170 seconds, 10° C. per 180 seconds, 10° C. per 190 seconds, or 10° C. per 200 seconds. In some embodiments, the temperature is maintained at a pre-determined temperature for a pre-determined amount of time. A rate of cooling in a temperature ramp-down phase is configured to improve cell viability. For example, certain cooling rates in a temperature ramp-down phase improves cell functionality post-cryopreservation. In some embodiments, cooling rates in a temperature ramp-down phase are configured to improve cell integrity or stability. In some embodiments, the cryopreserved cells substantially maintain therapeutic effect post-cryopreservation. For example, the cells are suitable for direct implantation at a target site of a patient post thawing of the cryopreserved cells with a yield of therapeutic efficacy roughly equivalent to (or better than) cells that have not been cryopreserved.

In some embodiments, the methods of cryopreserving includes one or more hold steps that last from about 1 minutes to about 10 minutes. In some embodiments, the hold step is for about 1 minute. In some embodiments, the hold step is for about 3 minutes. In some embodiments, the hold step is for about 5 minutes. In some embodiments, the hold step is for about 10 minutes. The hold steps can occur at various temperature. For example, in some embodiments, the hold step occurs at a temperature of about −2.0° C. In some embodiments, the hold step is at a temperature of about −25° C. In some embodiments, the hold step is at a temperature of about −40° C. In some embodiments, the hold step is at a temperature of about −60° C. In some embodiments, the methods of cryopreserving disclosed herein includes one, two, three, four, five or more hold steps. In some embodiments, the method includes one hold step. In some embodiment, the method includes two hold steps. In some embodiments, the method includes three hold steps. In some embodiments, the method includes four hold steps. In some embodiments, the method includes five hold steps. In some embodiments, the method includes more than five hold steps.

In some embodiments, the total time for the cryoprotection process is less than 120 minutes. In some embodiments, the total time for the cryoprotection process is less than 100 minutes. In some embodiments, the total time for the cryoprotection process is less than 90 minutes. In some embodiments, the total time for the cryoprotection process is about 60 minutes.

In some embodiments, the final temperature is about –80° C. In some embodiments the final temperature is below –80° C. In some embodiments, the final temperature is –90° C. In some embodiments, the final temperature is –96° C. In some embodiments, the final temperature is –120° C. In some embodiments, the final temperature is –196° C.

In some embodiments, the method of freezing as disclosed herein, encompasses a series of steps resulting in controlled change in temperature. In some embodiments, the method can comprises a series of steps that comprises decreasing the temperature. In some embodiments, the method comprises a series of steps that include increasing the temperature.

In some embodiments, a method of changing temperature of a sample containing cells from a first temperature to a final temperature of less than or equal to –80° C., thereby cryopreserving the sample at the final temperature, the method comprises the steps of (a) placing the sample at a first temperature above the freezing temperature of the sample; (b) reducing the first temperature to a second temperature at a first controlled rate, where the second temperature is at least 2° C. less than the first temperature; (c) reducing the second temperature to a third temperature at a second controlled rate, where the third temperature is at least 40° C. less than the second temperature; (d) increasing the third temperature to a fourth temperature at a third controlled rate, where the fourth temperature is at least 20° C. more than the third temperature; (e) reducing the fourth temperature to a fifth temperature at a fourth controlled rate, where the fifth temperature is at least 10° C. less than the fourth temperature; and (f) reducing the fifth temperature to the final temperature at a fifth controlled rate, where the final temperature is less than or equal to –80° C.

In some embodiments, the first temperature is about 4° C. to 0° C.

In some embodiments, the first controlled rate is between about 0.75° C. and 1.25° C. per minute.

In some embodiments, the second temperature is about –2° C.

In some embodiments, the second controlled rate is between about 20° C. and 30° C. per minute.

In some embodiments, the third temperature is about –60° C.

In some embodiments, the third controlled rate is between about 5° C. and 15° C. per minute.

In some embodiments, the fourth temperature is about –25° C.

In some embodiments, the fourth controlled rate is between 0.5° C. and 1.25° C. per minute.

In some embodiments, the firth temperature is about –40° C.

In some embodiments, the fifth controlled rate is between 7° C. and 15° C. per minute.

In some embodiments, final temperature is less than or equal to –80° C.

In some aspects, a method is provided comprising cryopreserving engineered immune cells suitable for cell therapy, the method comprising stepwise freezing a population of engineered immune cells at a controlled rate to minimize latent heat of fusion, where the stepwise freezing comprises cooling the cells at a rate of between 0.5° C. per minute to 30° C. per minute to a final temp of –80° C. or below, thereby to cryopreserving the cells.

In some aspects, a method of thawing the cryopreserved engineered immune cells includes heating a container comprising the cryopreserved engineered immune cells to a temperature of between 37° C. and 70° C.; and agitating the cells at a speed of between about 100 and about 250 RPM for a suitable period of time until the cells are thawed.

In some aspects, a method is provided comprising cryopreserving engineered immune cells suitable for cell therapy using a cryopreservation media described herein, the method comprising stepwise freezing a population of engineered immune cells at a controlled rate to minimize latent heat of fusion, where the stepwise freezing comprises cooling the cells at a rate of between 0.5° C. per minute to 30° C. per minute to a final temp of –80 or below, thereby cryopreserving the cells.

In some aspects, a method of thawing the cryopreserved engineered immune cells is provided, the method comprising heating a container comprising the cryopreserved engineered immune cells to a temperature of between 37° C. and 70° C.; and agitating the cells at a speed of between about 100 and about 250 RPM for a suitable period of time until the cells are thawed.

In some embodiments, the agitating the cells is at a speed of about between 100 RPM to about 250 RPM. In some embodiments, the agitating the cells is at a speed of about between 100 RPM to about 150 RPM. In some embodiments, the agitating the cells is at a speed of about between 100 RPM to about 125 RPM. In some embodiments, the agitating the cells is at a speed of about 100 RPM. In some embodiments, the agitating the cells is at a speed of about 125 RPM. In some embodiments, the agitating the cells is at a speed of about 150 RPM. In some embodiments, the agitating the cells is at a speed of about 200 RPM. In some embodiments, the agitating the cells is at a speed of about 250 RPM.

In some embodiments, the total time of thawing is about between 5 minutes and 20 minutes. Accordingly, in some embodiments, the total time of thawing is about 5 minutes. In some embodiments, the total time of thawing is about 10 minutes. In some embodiments, the total time of thawing is about 15 minutes. In some embodiments, the total time of thawing is about 20 minutes.

In a particular embodiment, the cryopreserved cells are CAR-NK cells which comprise cord blood derived NK cells that have been engineered to express a CD-19 CAR, an IL-15 and iCaspase9, which are cryopreserved using methods described herein and then thawed in an orbital shaker water bath for about 10 minutes at 60° C. and about 125 rpm. Once thawed, the cells may be administered to a subject in need thereof.

In some embodiments, the thawed cells are stable for between about 1 to 6 hours. Accordingly, in some embodiments, the thawed cells are stable for about between 2 to 4 hours. In some embodiments, the thawed cells are stable for about between 1 to 2 hours. In some embodiments, the thawed cells are stable for about 1 hour. In some embodiments, the thawed cells are sable for about 2 hours. In some embodiments, the thawed cells are stable for about 3 hours. In some embodiments, the thawed cells are stable for about 4 hours. In some embodiments, the thawed cells are stable for about 5 hours. In some embodiments, the thawed cells are stable for more than 5 hours.

In some embodiments, the thawed cells can be administered to a subject in need thereof during a period for which the thawed cells are stable. For example, in some embodiments, the thawed cells are administered to a patient in need thereof, within between about 30 minutes and 5 hours of thawing. In some embodiments, the thawed cells are administered to a patient in need thereof, within between about 30 minutes and 2 hours of thawing. In some embodiments, the thawed cells are administered to a patient in need thereof, immediately after thawing.

In several embodiments, the mammalian immune cells can be frozen for approximately 1-5 hours, 5-12 hours, 12-24 hours, 24-48 hours, 48 hours to one week, one week to two weeks, two to three weeks, three to four weeks or longer, and overlapping ranges thereof. In some embodiments, the cells are cryopreserved and stored for more than one month, for more than one year, more than 5 years, more than 10 years, or longer.

In some embodiments, the immune cells can be freshly isolated. In some embodiments, the immune cells are at least once-frozen and thawed.

In some embodiments, cryopreserved cells are thawed for use (e.g., implantation) by transferring a cryovial containing the cryopreserved cells to a water bath having a temperature around body temperature, for example a temperature of around 37° C., or any other suitable temperature. In other embodiments, a "step up" thawing process having a step up heating rate is used. For example, the cryovial may, in some embodiments, be placed in sequential storage environments with increasing temperatures before being transferred to a temperature that is around body temperature, for example a water bath having a temperature of 50° C. or more, or any other suitable temperature as described herein.

In several embodiments, the cells are thawed at patient bedside allowing for immediate use of the freshly-thawed cells. In several embodiments, after thawing the immune cells may be transferred to a culture dish and cultured under appropriate conditions for a period of approximately 30 minutes, one hour, 6 hours, 12 hours, 24 hours, 48 hours, 72 hours, 86 hours, 110 hours, one week, two weeks, or more than three weeks prior to being transported to the desired location (e.g., the operating room for delivery to a patient). Alternatively, in several embodiments, the thawed cell-seeded substrate is directly injected into a patient.

Methods of Thawing

Current methods of thawing cryopreserved cells are performed on cell suspensions of mammalian immune cells. In some embodiments, the thawing process is rapid and is scalable to up to 5 vials. In some embodiments, the thawing process is rapid and is scalable to up to 10 vials, 15 vials, 20 vials, 25 vials, 30 vials or more. As described above, slow thawing tends to cause physical damages to cells due to formation of ice crystals. Current methods of thawing encompass thawing immune cells in orbital shaker water bath or the like. In some embodiments, thawing can be accomplished by a dry-thawing device which can uniformly distribute heat throughout the cryopreserved samples to thaw the sample. In some embodiments, the thawing is accomplished by adjusting the temperature of the water bath to 40° C. In some embodiments, the thawing is accomplished by adjusting the temperature of the water bath to 45° C. In some embodiments, the thawing is accomplished by adjusting the temperature of the water bath to 50° C. In some embodiments, the thawing is accomplished by adjusting the temperature of the water bath to 55° C. In some embodiments, the thawing is accomplished by adjusting the temperature of the water bath to 60° C. In some embodiments, the thawing is accomplished by adjusting the temperature of the water bath to 65° C.

In some embodiments, the thawing is accomplished by adjusting the rotational speed of the orbital shaker water bath to between 100 rpm and 250 rpm. In some embodiments, the thawing is accomplished by adjusting the rotational speed of the orbital shaker water bath to 120 rpm. In some embodiments, the thawing is accomplished by adjusting the rotational speed of the orbital shaker water bath to 125 rpm. In some embodiments, the thawing is accomplished by adjusting the rotational speed of the orbital shaker water bath to 130 rpm. In some embodiments, the thawing is accomplished by adjusting the rotational speed of the orbital shaker water bath to 135 rpm. In some embodiments, the thawing is accomplished by adjusting the rotational speed of the orbital shaker water bath to 140 rpm. In some embodiments, the thawing is accomplished by adjusting the rotational speed of the orbital shaker water bath to 145 rpm. In some embodiments, the thawing is accomplished by adjusting the rotational speed of the orbital shaker water bath to 150 rpm. In some embodiments, the thawing is accomplished by adjusting the rotational speed of the orbital shaker water bath more than 150 rpm.

In some embodiments, the speed of agitation does not cause shearing of cells being thawed.

Figure 1B:
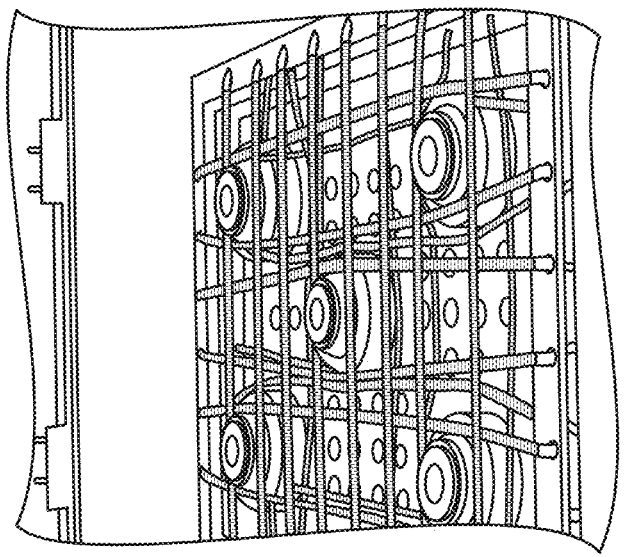
FIG. 1B is a diagram showing an exemplary sample chamber of an orbital shaker with holders for holding cryo-containers or vials for rapid thawing of cryopreserved cells.
Figure 1A:
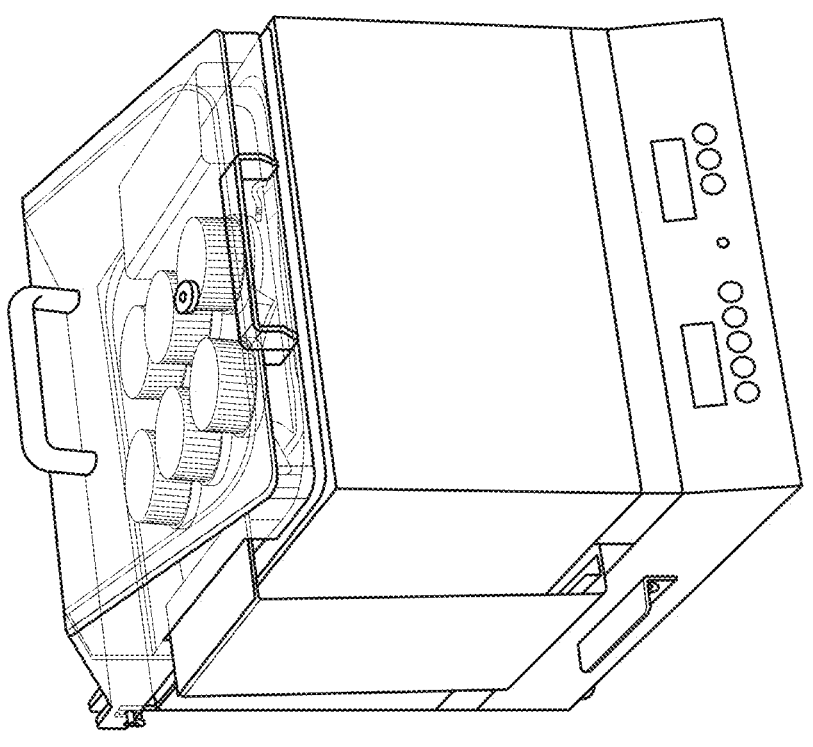
FIG. 1A is a diagram showing an exemplary orbital shaker water bath with adjustable rotational speed and temperature.

In some embodiments, the thawing is accomplished by adjusting the temperature of the orbital shaker water bath to 37° C. and the rotational speed to 100 rpm. In some embodiments, the thawing is accomplished by adjusting the temperature of the orbital shaker water bath to 37° C. and the rotational speed to 125 rpm. In some embodiments, the thawing is accomplished by adjusting the temperature of the orbital shaker water bath to 37° C. and the rotational speed to 150 rpm. In some embodiments, the thawing is accomplished by adjusting the temperature of the orbital shaker water bath to 37° C. and the rotational speed to 175 rpm. In some embodiments, the thawing is accomplished by adjusting the temperature of the orbital shaker water bath to 37° C. and the rotational speed to 200 rpm. In some embodiments, the thawing is accomplished by adjusting the temperature of the orbital shaker water bath to 45° C. and the rotational speed to 100 rpm. In some embodiments, the thawing is accomplished by adjusting the temperature of the orbital shaker water bath to 45° C. and the rotational speed to 125 rpm. In some embodiments, the thawing is accomplished by adjusting the temperature of the orbital shaker water bath to 45° C. and the rotational speed to 150 rpm. In some embodiments, the thawing is accomplished by adjusting the temperature of the orbital shaker water bath to 45° C. and the rotational speed to 175 rpm. In some embodiments, the thawing is accomplished by adjusting the temperature of the orbital shaker water bath to 45° C. and the rotational speed to 200 rpm. In some embodiments, the thawing is accomplished by adjusting the temperature of the orbital shaker water bath to 50° C. and the rotational speed to 100 rpm. In some embodiments, the thawing is accomplished by adjusting the temperature of the orbital shaker water bath to 50° C. and the rotational speed to 125 rpm. In some embodiments, the thawing is accomplished by adjusting the temperature of the orbital shaker water bath to 50° C. and the rotational speed to 150 rpm. In some embodiments, the thawing is accomplished by adjusting the temperature of the orbital shaker water bath to 50° C. and the rotational speed to 175 rpm. In some embodiments, the thawing is accomplished by adjusting the temperature of the orbital shaker water bath to 50° C. and the rotational speed to 200 rpm. In some embodiments, the thawing is accomplished by adjusting the temperature of the orbital shaker water bath to 60° C. and the rotational speed to 100 rpm. In some embodiments, the thawing is accomplished by adjusting the temperature of the orbital shaker water bath to 60° C. and the rotational speed to 125 rpm. In some embodiments, the thawing is accomplished by adjusting the temperature of the orbital shaker water bath to 60° C. and the rotational speed to 150 rpm. In some embodiments, the thawing is accomplished by adjusting the temperature of the orbital shaker water bath to 60° C. and the rotational speed to 175 rpm. In some embodiments, the thawing is accomplished by adjusting the temperature of the orbital shaker water bath to 60° C. and the rotational speed to 200 rpm. An exemplary orbital shaker is shown in FIG. 1A-1B.

In some embodiments, the thawing is accomplished by adjusting the temperature of the dry heating device to 37° C. and the rotational speed to 100 rpm. In some embodiments, the thawing is accomplished by adjusting the temperature of the dry heating device to 37° C. and the rotational speed to 125 rpm. In some embodiments, the thawing is accomplished by adjusting the temperature of the dry heating device to 37° C. and the rotational speed to 150 rpm. In some embodiments, the thawing is accomplished by adjusting the temperature of the dry heating device to 37° C. and the rotational speed to 175 rpm. In some embodiments, the thawing is accomplished by adjusting the temperature of the dry heating device to 37° C. and the rotational speed to 200 rpm. In some embodiments, the thawing is accomplished by adjusting the temperature of the dry heating device to 45° C. and the rotational speed to 100 rpm. In some embodiments, the thawing is accomplished by adjusting the temperature of the dry heating device to 45° C. and the rotational speed to 125 rpm. In some embodiments, the thawing is accomplished by adjusting the temperature of the dry heating device to 45° C. and the rotational speed to 150 rpm. In some embodiments, the thawing is accomplished by adjusting the temperature of the dry heating device to 45° C. and the rotational speed to 175 rpm. In some embodiments, the thawing is accomplished by adjusting the temperature of the dry heating device to 45° C. and the rotational speed to 200 rpm. In some embodiments, the thawing is accomplished by adjusting the temperature of the dry heating device to 50° C. and the rotational speed to 100 rpm. In some embodiments, the thawing is accomplished by adjusting the temperature of the dry heating device to 50° C. and the rotational speed to 125 rpm. In some embodiments, the thawing is accomplished by adjusting the temperature of the dry heating device to 50° C. and the rotational speed to 150 rpm. In some embodiments, the thawing is accomplished by adjusting the temperature of the dry heating device to 50° C. and the rotational speed to 175 rpm. In some embodiments, the thawing is accomplished by adjusting the temperature of the dry heating device to 50° C. and the rotational speed to 200 rpm. In some embodiments, the thawing is accomplished by adjusting the temperature of the dry heating device to 60° C. and the rotational speed to 100 rpm. In some embodiments the thawing is accomplished by adjusting the temperature of the dry heating device to 60° C. and the rotational speed to 125 rpm. In some embodiments, the thawing is accomplished by adjusting the temperature of the dry heating device to 60° C. and the rotational speed to 150 rpm. In some embodiments, the thawing is accomplished by adjusting the temperature of the dry heating device to 60° C. and the rotational speed to 175 rpm. In some embodiments the thawing is accomplished by adjusting the temperature of the dry heating device to 60° C. and the rotational speed to 200 rpm.

In some embodiments, the thawing is accomplished by incubating the cryopreserved cell suspension in the orbital shaker water bath for about 5 min. In some embodiments, the thawing is accomplished by incubating the cryopreserved cell suspension in the orbital shaker water bath for about 6 min. In some embodiments, the thawing is accomplished by incubating the cryopreserved cell suspension in the orbital shaker water bath for about 7 min. In some embodiments, the thawing is accomplished by incubating the cryopreserved cell suspension in the orbital shaker water bath for about 8 min. In some embodiments, the thawing is accomplished by incubating the cryopreserved cell suspension in the orbital shaker water bath for about 9 min. In some embodiments, the thawing is accomplished by incubating the cryopreserved cell suspension in the orbital shaker water bath for about 10 min. In some embodiments, the thawing is accomplished by incubating the cryopreserved cell suspension in the orbital shaker water bath for about 11 min. In some embodiments, the thawing is accomplished by incubating the cryopreserved cell suspension in the orbital shaker water bath for about 12 min. In some embodiments, the thawing is accomplished by incubating the cryopreserved cell suspension in the orbital shaker water bath for about 13 min. In some embodiments, the thawing is accomplished by incubating the cryopreserved cell suspension in the orbital shaker water bath for about 14 min. In some embodiments, the thawing is accomplished by incubating the cryopreserved cell suspension in the orbital shaker water bath for about 15 min.

In some embodiments, the thawing is accomplished by incubating the cryopreserved cell suspension in the dry heating device for about 5 min. In some embodiments, the thawing is accomplished by incubating the cryopreserved cell suspension in the dry heating device for about 6 min. In some embodiments, the thawing is accomplished by incubating the cryopreserved cell suspension in the dry heating device for about 7 min. In some embodiments, the thawing is accomplished by incubating the cryopreserved cell suspension in the dry heating device for about 8 min. In some embodiments, the thawing is accomplished by incubating the cryopreserved cell suspension in the dry heating device for about 9 min. In some embodiments, the thawing is accomplished by incubating the cryopreserved cell suspension in dry heating device for about 10 min. In some embodiments, the thawing is accomplished by incubating the cryopreserved cell suspension in the dry heating device for about 11 min. In some embodiments, the thawing is accomplished by incubating the cryopreserved cell suspension in dry heating device for about 12 min. In some embodiments, the thawing is accomplished by incubating the cryopreserved cell suspension in the dry heating device for about 13 min. In some embodiments, the thawing is accomplished by incubating the cryopreserved cell suspension in the dry heating device for about 14 min. In some embodiments, the thawing is accomplished by incubating the cryopreserved cell suspension in the dry heating device bath for about 15 min.

Thawing cells in this manner, such as for example CAR-NK cells, allows for thawed cells to retain high viability (e.g., greater than 70%, 75%, 80%, 85%, 90%, 95%, or greater than 95%) and functionality similar to cells that have not been cryopreserved following CAR transduction.

Measurement of Cell Freeze-Thaw Efficacy

In some embodiments, the freeze-thaw efficacy is measured by measuring cell viability using, for example, by staining dead cells to distinguish from live cells. In some embodiments, the freeze-thaw efficacy is measured by measuring metabolic activity, ATP content, or cell proliferation. Any suitable assay for measuring cell viability can be used to assess cell viability. In some embodiments, the freeze-thaw is effective if cell viability is greater than 50%. In some embodiments, the freeze-thaw is effective if cell viability is greater than 60%. In some embodiments freeze-thaw is effective if cell viability is greater than 70%. In some embodiments, the freeze-thaw is effective if cell viability is greater than 80%. In some embodiments, the freeze-thaw is effective if cell viability is greater than 90%.

In some embodiments, the freeze-thaw efficacy is measured by measuring percent killing of a target at a given effector to target (E:T) ratio. E:T ratio is a given amount of T cells (effector cells) taken, to amount of target cells. In some embodiments, the freeze-thaw is effective if the percent target killing is at a particular E:T ratio in comparison to a freshly isolated cell sample E:T ratio.

Methods of Use of Cryopreservation

In some embodiments, the cryopreservation procedure is used in connection with transporting therapeutic cells to a destination of use. In some embodiments, to avoid devitrification, cryopreserved cells are transported in liquid nitrogen dry shippers, e.g., at a temperature ranging from −140° C. to −196° C. Accordingly, in some embodiments, the cryopreserved cells are transported in a cryoshipping container. In some embodiments, vitrified cells are shipped in a sterile container and/or in a sterile environment. In some embodiments, vitrified cells are transported to locations, for example hospitals or cell banks, in large scale. In some embodiments, the cryopreservation techniques described herein are compatible with vapor phase storage for 96 hours under "transport conditions" do not adversely affect the viability after warming. In some embodiments, the cryopreserved cells are thawed at patient bedside.

Cryopreservation Media

Provided herein are various cryopreservation media suitable for cryopreserving cells. In some embodiments, the cryopreservation media provided herein is suitable for cryopreserving immune cells. Various immune cells are known, and include for example NK cells; T cells including alpha beta T cells, gamma delta T cells and regulatory T cells; B cells; HSCs; and MSCs. In one embodiment, the immune cells are cord blood derived NK cells, iPS cell derived NK cells and iPS cell derived T cells. In one embodiment, the cells are NK cells, in particular, allogeneic NK cells expressing a CAR (i.e., CAR-NK cells).

In some aspects, a suitable cryopreservation medium for cryopreserving and subsequent thawing of viable cells comprises: a cryoprotectant, an albumin and a non-pyrogenic and isotonic crystalloid solution. In some aspects, a suitable cryopreservation medium for cryopreserving and subsequent thawing of viable cells comprises: a cryoprotectant, a disaccharide, an albumin and a non-pyrogenic and isotonic crystalloid solution.

Various cryoprotectants are known in the art and include, for example, dimethyl sulfoxide (DMSO), glycerol, and propanediol among others. In some embodiments, the cryopreservation medium comprises DMSO as a cryoprotectant. In some embodiments, human serum albumin (HSA) is the albumin in the cryopreservation medium.

In some embodiments, the suitable cryopreservation medium also comprises a saccharide or a sugar. In another aspects, a suitable cryopreservation medium comprises: HSA, sodium, sodium chloride, sodium gluconate, sodium acetate trihydrate, potassium chloride, magnesium chloride, dimethyl sulfoxide (DMSO), and a disaccharide.

In some embodiments, a saccharide includes a monosaccharide, a disaccharide, a trisaccharide or a polysaccharide. In some embodiments, the saccharide is a disaccharide. In some embodiments, the disaccharide is sucrose, lactose, maltose, trehalose, cellobiose, or chitobiose. In some embodiments, the disaccharide is trehalose.

In some embodiments, a suitable cryopreservation medium incudes one or more of glucose, xylose, arabinose, fructose, galactose, mannose, mannitol, sorbitol, xylitol, myoinositol, trehalose, sucrose, lactose, maltose, cellobiose, lactitol, maltitol, methyl cellulose, carboxymethyl cellulose, dextran, glycogen, amylose, amylopectin, inulin, sodium alginate, ethyl cellulose, hydroxyethyl cellulose, raffinose, stachyose, xanthan gum, glucosamine, and galactosamine. In some embodiments, a suitable cryopreservation medium includes trehalose, sucrose, mannitol, and/or dextran. In some embodiments, a suitable cryopreservation medium incudes one or more sugars selected from trehalose, sucrose and/or mannitol.

Various concentration of saccharides or sugar can be used in a cryopreservation medium. In some embodiments, the cryopreservation medium includes trehalose, sucrose, or mannitol between about 0 mM-500 mM. In some embodiments, the cryopreservation medium includes trehalose, sucrose, or mannitol between about 0 mM-200 mM. In some embodiments, the cryopreservation medium includes trehalose, sucrose, or mannitol between about 0 mM-100 mM.

In some embodiments, the cryopreservation media includes one or more sugars selected from trehalose, sucrose and/or mannitol at a concentration of between about 0-100 mM. In some embodiments, the cryopreservation medium includes mannitol between about 0-100 mM.

In some embodiments, the cryopreservation medium includes trehalose between about 10 mM-100 mM. In some embodiments, the cryopreservation medium includes 30 mM trehalose.

Accordingly, in some embodiments, trehalose, sucrose, or mannitol is present in the cryopreservation medium at a final concentration of about 1 mM, 5 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 105 mM, 110 mM, 115 mM, 120 mM, 125 mM, 130 mM, 135 mM, 140 mM, 145 mM, 150 mM, 155 mM, 160 mM, 165 mM, 170 mM, 175 mM, 180 mM, 185 mM, 190 mM, 195 mM, or 200 mM.

Accordingly, in some embodiments, trehalose, sucrose, or mannitol is present in the cryopreservation medium at a final concentration of less than 1 mM, less than 10 mM, less than 20 mM, less than 30 mM, less than 40 mM, less than 50 mM, less than 60 mM, less than 70 mM, less than 80 mM, less than 90 mM, less than 100 mM, less than 110 mM, less than 120 mM, less than 130 mM, less than 140 mM, less than 150 mM, less than 160 mM, less than 170 mM, less than 180 mM, less than 190 mM, or less than 200 mM.

In some embodiments, the cryopreservation medium includes a dextran. In some embodiments, the cryopreservation medium includes a dextran between about 0-20 w/v %. In some embodiments, the cryopreservation medium includes a dextran between about 0-6 w/v %. Accordingly, in some embodiments, dextran is present in the cryopreservation medium at a final concentration of about 0.2 w/v %, 0.4 w/v %, 0.6 w/v %, 0.8 w/v %, 1.0 w/v %, 1.5 w/v %, 2.0 w/v %, 2.5 w/v %, 3.0 w/v %, 3.5 w/v %, 4.0 w/v %, 4.5 w/v %, 5.0 w/v %, 5.5 w/v %, 6.0 w/v %, 6.5 w/v %, 7.0 w/v %, 7.5 w/v %, 8.0 w/v %, 8.5 w/v %, 9.0 w/v %, 9.5 w/v %, 10.0 w/v %, 10.5 w/v %, 11.0 w/v %, 11.5 w/v %, 12.0 w/v %, 12.5 w/v %, 13.0 w/v %, 13.5 w/v %, 14.0 w/v %, 14.5 w/v %, 15.0 w/v %, 15.5 w/v %, 16.0 w/v %, 16.5 w/v %, 17.0 w/v %, 17.5 w/v %, 18.0 w/v %, 18.5 w/v %, 19.0 w/v %, 19.5 w/v %, or 20.0 w/v %.

In some embodiments, the cryopreservation medium comprises a non-pyrogenic and isotonic crystalloid solution. Various non-pyrogenic and isotonic crystalloid solutions can be used in the cryopreservation medium described herein. For example, exemplary isotonic crystalloid solutions can be used in the cryopreservation media include PLASMA-LYTE A, normal saline, a lactate buffered solution, an acetate buffered solution, an acetate and lactate buffered solution, and a dextrose in water solution. Generally, non-pyrogenic and isotonic crystalloid solutions comprise one or more of the following sodium chloride, sodium gluconate, sodium acetate trihydrate, potassium chloride, and magnesium chloride. Accordingly, in some embodiments, the cryopreservation medium comprises one or more of the following sodium chloride, sodium gluconate, sodium acetate trihydrate, potassium chloride, and magnesium chloride. In some embodiments, following sodium chloride, sodium gluconate, sodium acetate trihydrate, potassium chloride, and magnesium chloride. An example of a commercially available non-pyrogenic and isotonic crystalloid solutions is PLASMA-LYTE A. In some embodiments, the non-pyrogenic and isotonic crystalloid solution is PLASMA-LYTE A. In some embodiments, the non-pyrogenic and isotonic crystalloid solution is a 0.9% normal saline solution. In some embodiments, the non-pyrogenic and isotonic crystalloid solution is a lactate buffered solution. In some embodiments, the non-pyrogenic and isotonic crystalloid solution is a dextrose in water solution.

PLASMA-LYTE A includes sodium chloride, sodium gluconate, sodium acetate trihydrate, potassium chloride, and magnesium chloride. In some embodiments, the cryopreservation medium includes between about 10% v/v-75% v/v Plasma-LYTE A. In some embodiments, the cryopreservation medium includes between about 25% v/v-50% v/v PLASMA-LYTE A. In some embodiments, the cryopreservation medium includes between about 40% v/v PLASMA-LYTE A. Accordingly, in some embodiments, the cryopreservation medium includes about 10% v/v, 15% v/v, 20% v/v, 25% v/v, 30% v/v, 35% v/v, 40% v/v, 45% v/v, 50% v/v, 55% v/v, 60% v/v, 65% v/v, 70% v/v, or 75% v/v PLASMA-LYTE A.

In some embodiments, the cryopreservation medium includes sodium chloride between about 0.1 mg/mL to about 1 mg/mL. In some embodiments, the cryopreservation medium includes sodium chloride between about 0.4 mg/mL to about 0.6 mg/mL. Accordingly, in some embodiments, the cryopreservation medium includes about 0.1 mg/mL, 0.15 mg/mL, 0.2 mg/mL, 0.25 mg/mL, 0.3 mg/mL, 0.35 mg/mL, 0.4 mg/mL, 0.45 mg/mL, 0.5 mg/mL, 0.55 mg/mL, 0.6 mg/mL, 0.65 mg/mL, 0.7 mg/mL, 0.75 mg/mL, 0.8 mg/mL, 0.85 mg/mL, 0.9 mg/mL, 0.95 mg/mL, 1 mg/mL sodium chloride.

In some embodiments, the cryopreservation medium includes sodium gluconate between about 0.1 mg/mL to about 1 rng/mL. In some embodiments, the cryopreservation medium includes sodium gluconate between about 0.3 mg/mL to about 0.6 mg/mL. Accordingly, in some embodiments, the cryopreservation medium includes about 0.1 mg/mL, 0.15 mg/mL, 0.2 mg/mL, 0.25 mg/mL, 0.3 mg/mL, 0.35 mg/mL, 0.4 mg/mL, 0.45 mg/mL, 0.5 mg/mL, 0.55 mg/mL, 0.6 mg/mL, 0.65 mg/mL, 0.7 mg/mL, 0.75 mg/mL, 0.8 mg/mL, 0.85 mg/mL, 0.9 mg/mL, 0.95 mg/mL, 1 mg/mL sodium gluconate.

In some embodiments, the cryopreservation medium includes between about 25% v/v-75% v/v CS10, In some embodiments, the cryopreservation medium includes between about 40% v/v-60% v/v CS10. In some embodiments, the cryopreservation medium includes about 50% v/v CS10. Accordingly, in some embodiments, the CS10 is present in the cryopreservation medium at about 25% v/v, 30% v/v, 35% v/v, 40% v/v, 45% v/v, 50% v/v, 55% v/v, 60% v/v, 65% v/v, 70% v/v, or 75% v/v. In some embodiments, the CS10 comprises dimethyl sulfoxide (DMSO).

In some embodiment, the cryopreservation medium comprises human serum albumin (HSA). In some embodiments, the cryopreservation medium includes between about 0.5 v/v %-25 v/v % I-IS A. In some embodiments, the cryopreservation medium includes between about 5 v/v %-20 v/v % HSA. In some embodiments, the cryopreservation medium includes about 10 v/v % HSA. In some embodiments, the cryopreservation medium includes about 1.25% v/v to 5% v/v HSA. In some embodiments, the cryopreservation medium includes about 2.5% v/v HSA.

Accordingly, in some embodiments, the cryopreservation medium includes about 0.5 v/v %, 1.0 v/v %, 1.5 v/v %, 2.0 v/v %, 2.5 v/v %, 3.0 v/v %, 3.5 v/v %, 4.0 v/v %, 4.5 v/v %, 5.0 v/v %, 6.0 v/v %, 6.5 v/v %, 7.0 v/v %, 7.5 v/v %, 8.0 v/v %, 8.5 v/v %, 9.0 v/v %, 10.0 v/v %, 10.5 v/v %, 11.0 v/v %, 11.5 v/v %, 12.0 v/v %, 12.5 v/v %, 13.0 v/v %, 13.5 v/v %, 14.0 v/v %, 14.5 v/v %, 15.0 v/v %, 15.5 v/v %, 16.0 v/v %, 16.5 v/v %, 17.0 v/v %, 17.5 v/v %, 18.0 v/v %, 18.5 v/v %, 19.0 v/v %, 19.5 v/v %, 20.0 v/v %, 20.5 v/v %, 21.0 v/v %, 21.5 v/v %, 22.0 v/v %, 22.5 v/v %, 23.0 v/v %, 23.5 v/v %, 24.0 v/v %, 24.5 v/v %, or 25.0 v/v % HSA.

In some aspects, the cryopreservation medium comprises one or more of HSA, $Ca^{2+}$, $Na^+$, $K^+$, $Mg^{2+}$, HEPES, one or more disaccharides, a sugar alcohol, dextran, a metabolite, and an anti-oxidant. In another aspects, the cryopreservation medium comprises: HSA, $Na^+$, $K^+$, $Mg^{2+}$, HEPES (4-(2-hydroxyethyl)-1-piperazineethanesulfonic acid) at a concentration of about 0-55 mM, one or more sugars selected from trehalose, sucrose and/or mannitol at a concentration of between about 0-100 mM, dextran between about 0-6%, adenosine, and glutathione. In some embodiments, the metabolite is adenosine. In some embodiments, the anti-oxidant is glutathione.

Accordingly, in some embodiments, the HEPES is present in the cryopreservation medium at about 0 mM, 0.5 mM, 1 mM, 5 mM, 10 mM, 15 mM, 20 mM, 25 mM, 30 mM, 35 mM, 40 mM, 45 mM, 50 mM, or 55 mM.

In some embodiments, the cryopreservation medium comprises human serum albumin (HSA), PLASMA-LYTE A, and CS10.

In some aspects, the cryopreservation medium is suitable for cryopreserving natural killer (NK) cells. In some embodiments, the NK cells are from primary cell isolates. In some embodiments, the NK cells are cord blood derived NIK cells. In some embodiments, the NK cells are from a cell line. In some embodiments, the NK cells are fresh cells. In some embodiments, the NK cells were previously frozen and thawed, for example, the NK cells were previously frozen and thawed cord blood-derived NK cells. In some embodiments, the NK cells comprise a chimeric antigen receptor (CAR), such as for example CD19 CAR. In some embodiments, the cryopreservation medium comprises NK cells at a concentration of between 6 M/mL to 120 M/mL.

In some embodiments, a CAR-NK cell therapy product is cryopreserved using the formulations described herein. In some embodiments, the CAR-NK cell therapy product is an allogeneic cell therapy product comprised of human cord blood-derived NK cells transduced with a retroviral vector expressing iCaspase9, CD-19 CAR and IL-15.

In some embodiments, a CAR-NK cell therapy product comprises an anti-CD19 binding domain comprising a light chain variable region comprising the amino acid sequence set forth in SEQ ID NO: 1 and/or a heavy chain variable region listed in SEQ ID NO: 2. In another embodiment, the CD-19 CAR can include an anti-CD19 binding domain, a CD28 transmembrane domain (an exemplary CD28 transmembrane sequence is shown in SEQ ID NO: 3, a CD3z signaling domain (an exemplary CD3z sequence is shown in SEQ ID NO: 4 and can further include a suicide switch such as iCaspase9 and/or IL-15.

In one embodiment, a CAIR-NK cell therapy product includes a nucleic acid molecule encoding the heavy chain variable region of an anti-CD19 binding domain and/or a nucleic acid molecule encoding the light chain variable region of an anti-CD19 binding domain.

Accordingly, in some embodiments, the cryopreservation medium comprises NK cells at a concentration of about 1 M/mL, 5 M/mL, 10 M/mL, 15 M/mL, 20 M/mL, 25 M/mL, 30 M/mL, 35 M/mL, 40 M/mL, 45 M/mL, 50 M/mL, 55 M/mL, 60 M/mL, 65 M/mL, 70 M/mL, 75 M/mL, 80 M/mL, 85 M/mL, 90 M/mL, 95 M/mL, 100 M/mL, 105 M/mL, 110 M/mL, 115 M/mL, 120 M/mL, 130 M/mL, 140 M/mL, 150 M/mL, 160 M/mL, 170 M/mL, 180 M/mL, 190 M/mL, 200 M/mL.

In some embodiments, the genetically engineered cord blood NK cells are present at a concentration of between 6 M/mL to 120 M/mL. In some embodiments, the genetically engineered cord blood NK cells are present at a concentration of between 6 M/mL to 200 M/mL. In some embodiments, the genetically engineered cord blood NK cells are present at a concentration of between 6 M/mL to 25 M/mL. In some embodiments, the genetically engineered cord blood NK cells are present at a concentration of between 6 M/mL to 120 M/mL in a volume of medium ranging from 30-45 ml. In some embodiments, the genetically engineered cord blood NK cells are present at a concentration of between 6 M/mL to 200 M/mL in a volume of medium ranging from 30-45 ml. In some embodiments, the genetically engineered cord blood NK cells are present at a concentration of between 6 M/mL to 25 M/mL in a volume of medium ranging from 30-45 ml.

In some embodiments, CAR-NK cells are formulated in a cryopreserved media provided herein at a concentration ranging from 100 million cells to 900 million cells, present in a volume of medium ranging from 30-45 mL. In a particular embodiments, CAR-NK cells are present at a concentration of about 200 million cells in a volume of about 36 mL of media. In another embodiments, CAR-NK cells are present at a concentration of about 800 million cells in a volume of about 36 mL of media. In some embodiments, cells in 36 mL of media are contained in an aseptic container (e.g., an AT vial).

In some embodiments, the NK cells comprise a CAR-NK cell therapy product comprising a population of cells between about $100 \times 10^6$ cells and about $900 \times 10^6$ formulated in a cryopreservation media described herein. In some embodiments, the NK cells comprise a CAR-NK cell therapy product comprising a population of cells ranging from $200 \times 10^6$ cells to about $800 \times 10^6$ formulated in a cryopreservation media described herein. In some embodiments, the CAR-NK cell therapy product is an allogeneic cell therapy product comprised of human cord blood-derived NK cells transduced with a retroviral vector expressing iCaspase9, CD19 CAR and IL-15. In a particular embodiment, CAR-NK cell therapy product is an allogeneic cell therapy product comprised of human cord blood-derived NK cells transduced with a retroviral vector expressing iCaspase9, CD19 CAR and IL-15, where the transduced cells are formulated at a concentration of 6M to 120M cells/mL in 36 ml of a cryopreserved media comprising DMSO, trehalose, HSA and PLASMA-LYTE A. In another embodiment, CAR-NK cell therapy product is an allogeneic cell therapy product comprised of human cord blood-derived NK cells transduced with a retroviral vector expressing iCaspase9, CD19 CAR and IL-15, where the transduced cells are formulated at a concentration of $800 \times 10^6$ cells in 36 ml of a cryopreserved media comprising DMSO, trehalose, HSA and PLASMA-LYTE A. In some embodiments, the transduced cells are frozen using a method described herein after they are suspended in the cryopreservation medium. The frozen cells can then be shipped or transported in a cryoshipper (e.g., at a temperature ranging from −140° C. to −196° C.) to a point of care location and administered to a subject in need thereof (e.g., a cancer patient) subsequent to thawing the cells using a method described herein.

Uses of Cryopreserved Cells

The methods and compositions described herein, including the CAR-NK cell compositions are suitable for adoptive cell therapy. Adoptive cell therapies can be used to treat various disease, including, for example, cancer. In certain embodiments, the frozen and subsequently thawed CAR-NK cell compositions contained within the cryopreservation medium described herein is useful for the treatment of a cancer or a tumor. In certain embodiments, the cancer comprises breast, heart, lung, small intestine, colon, spleen, kidney, bladder, head, neck, ovarian, prostate, brain, pancreatic, skin, bone, bone marrow, blood, thymus, uterine, testicular, and liver tumors. In some embodiments, the cancer is a blood cancer. In some embodiments, the blood cancer is a B-cell malignancy (e.g., diffuse large B-cell lymphonma).

In some embodiments, the methods described herein are useful for adoptive cell therapy. Accordingly, in some embodiment, cells described herein are cryopreserved and thawed in accordance with the descriptions provided herein. In some embodiments, the cells are NK as described herein. In some embodiments, the NK cells are suspended in cryopreservation media as described herein.

In some embodiments, the CAR-NK cell compositions suspended in the cryopreservation media described herein is used to treat a subject who has cancer. In some embodiments, the subject is administered a composition comprising CAR-NK cells within the cryopreservation media described herein. In some embodiments, the CAR-NK cell comprises an anti-CD19 CAR gene and an IL-15 gene. In some embodiments, the CAR-NK cell comprises an anti-CD19 CAR gene, an IL-15 gene, and iCaspase9. In some embodiments, the CAR-NK cells are not washed prior to administering to a subject in need thereof. In some embodiments, the CAR-NK cells are washed of the cryopreservation media prior to administering to a subject in need thereof.

In some embodiments, the adoptive cell therapy is used in combination with one or more additional cancer treatments, such as for example lymphodepleting chemotherapy. Accordingly, in some embodiments, a subject who has cancer receives lymphodepleting chemotherapy before administration of a CAR-NK cell therapy product formulated in a cryopreservation media described herein.

In some embodiments, a CAR-NK cell therapy product is cryopreserved as described herein and subsequently thawed prior to administration to a patient in need thereof. For example, a CAR-NK cell therapy product as described herein is cryopreserved, transported, thawed, and administered to a patient in need thereof as described herein. Accordingly, in some embodiments, the CAR-NK cell therapy product is cryopreserved in a formulation as described herein and subsequently thawed prior to administration to a patient for treatment of B-cell malignancies.

In some embodiments, the frozen CAR-NK cell therapy product is frozen and transported as described herein to a patient in need thereof. For example, in some embodiments, a method of transporting the cell therapy product comprises: (a) contacting the CAR-NK cells with a cryopreservation medium as described herein; (b) cooling the CAR-NK cells to a temperature of $-80^\circ$ C., thereby cryopreserving the mammalian cells; and (c) transporting the cryopreserved mammalian cells to a different location at a temperature of between about $-20^\circ$ C. to about $-190^\circ$ C. or below. In some embodiments, the cells are stored and transported at or less than about $-190^\circ$ C., and particular embodiment, at or below $-140^\circ$ C. In some embodiments, the transported cells may be stored in a cryo-shipper until administration to a patient.

In a particular embodiments, the cells used for adoptive cell therapy are cryopreserved in a vial (e.g., a 50 ml AT vial) at a concentration of 200-800 million cells in a volume of 36 ml of cryopreservation media. In various embodiments, the vial may be labeled after the cells are frozen and shipped with the label in a cryoshipper to a point of care location. In some embodiments, the vial may be labeled prior to freezing the cells.

In some embodiments, the cell therapy product is a CD19 CAR NK cells that further comprises IL-15 and iCaspase9. In some embodiments, the cell therapy product is cryopreserved in a container at concentration of between about 6 and 120 million cells per milliliter. In some embodiments, the cell therapy product is cryopreserved in a 50 mL container at concentration of between about 6 and 120 million cells per milliliter. In some embodiments, the cell therapy product is cryopreserved in a 50 mL container at concentration of between about 3 and 150 million cells per milliliter. In some embodiments, the cell therapy product is cryopreserved in a 50 mL container at concentration of between about 1 and 250 million cells per milliliter. In some embodiments, the cell therapy product is cryopreserved in a 50 mL container at concentration of between about 1 and 350 million cells per milliliter. In some embodiments, the cell therapy product is cryopreserved in a 50 mL container at a concentration of between about 1 and 500 million cells per milliliter.

In some embodiments, the cell therapy product comprises between about $20\times10^6$ and $100\times10^7$ cells in 50 mL container. In some embodiments, the cell therapy product comprises between about $100\times10^6$ and $900\times10^6$ cells in 50 mL container. In some embodiments, the cell therapy product comprises about $50\times10^6$ cells in 50 mL container. In some embodiments, the cell therapy product comprises about $100\times10^6$ cells in 50 mL container. In some embodiments, the cell therapy product comprises about $200\times10^6$ cells in 50 mL container. In some embodiments, the cell therapy product comprises about $100\times10^6$ cells in 50 mL container. In some embodiments, the cell therapy product comprises about $200\times10^6$ cells in 50 mL container. In some embodiments, the cell therapy product comprises about $300\times10^6$ cells in 50 mL container. In some embodiments, the cell therapy product comprises about $400\times10^6$ cells in 50 mL container. In some embodiments, the cell therapy product comprises about $500\times10^6$ cells in 50 mL container. In some embodiments, the cell therapy product comprises about $600\times10^6$ cells in 50 mL container. In some embodiments, the cell therapy product comprises about $700\times10^6$ cells in 50 mL container. In some embodiments, the cell therapy product comprises about $800\times10^6$ cells in 50 mL container. In some embodiments, the cell therapy product comprises about $900\times10^6$ cells in 50 mL container. In some embodiments, the cell therapy product comprises about $100\times10^7$ cells in 50 mL container.

In some embodiments, the cell therapy product is contained in a 50 mL container at a fill volume of about between 20-45 mL. In some embodiments, the cell therapy product is contained in a 50 mL container at a fill volume of about 36 mL. In some embodiments, the cell therapy product is an immune cell, such as an NK cell, T cell or B cell. In some embodiments, the immune cell is engineered to comprise one or more transgenes, for example a chimeric antigen receptor (CAR). In some embodiments, the cells are CAR-NK+ cells. In some embodiments, the cell therapy product comprises a CD19 CAR, IL-15 transgene and an iCaspas9. In some embodiments, the cell therapy product comprises between about $100\times10^6$ and $900\times10^6$ CAR-NK+ cells in a 50-ml container. In some embodiments, the amount of cell therapy product present is $100\times10^6$ CAR-NK+ cells in a 50-ml container. In some embodiments, the amount of cell therapy product present is $200\times10^6$ CAR-NK+ cells in a 50-ml container. In some embodiments, the amount of cell therapy product present is $300\times10^6$ CAR-NK+ cells in a 50-ml container. In some embodiments, the amount of cell therapy product present is $400\times10^6$ CAR-NK+ cells in a 50-ml container. In some embodiments, the amount of cell therapy product present is $500\times10^6$ CAR-NK+ cells in a 50-ml container. In some embodiments, the amount of cell therapy product present is $600\times10^6$ CAR-NK+ cells in a 50-ml container. In some embodiments, the amount of cell therapy product present is $700\times10^6$ CAR-NK+ cells in a 50-ml container. In some embodiments, the cell therapy product present is $800\times10^6$ CAR-NK+ cells in a 50-ml container. In some embodiments, the cell therapy product present is $900\times10^6$ CAR-NK+ cells in a 50-ml container. In some embodiments, the amount of cell therapy product present is $100\times10^7$ CAR-NK+ cells in a 50-ml container.

The transported cell therapy product can be thawed as described herein followed by administration to a patient in need thereof. In some embodiments, the cell therapy product is thawed at the patient's bedside. In some embodiments, the cell therapy product is not washed prior to administration into a patient in need thereof. In some embodiments, the thawed cells are administer into a patient in need thereof within about 30 minutes and 2 hours from thawing the cells. In some embodiments, the rate of infusion into a subject is between about 2-3 minutes.

In some embodiments, the transported cell therapy product remains frozen for further storage at the different location. In some embodiments, the thawed cells is introduced into a subject in need thereof without separating the cells and the cryopreservation solution. Thus, in some embodiments, the thawed cells are not washed prior to use. The thawed cells and accompanying cryopreservation solution is preferably warmed to body temperature (i.e., about $37^\circ$ C.) prior to introduction into the subject. In such situation, the dose of the cells is based on the pre-freeze cell count.

In some embodiments, thawed cells are further cultured. In some embodiments, culturing involves placing the cells in an incubator; removing the buffer solution; and replacing the buffer solution with a culture medium designed for the growth and/or differentiation of cells. In some embodiments, the cells are incubated in the incubator for between about 6 to 7 hours. In some embodiments, the culture medium designed for the growth and/or differentiation of cells comprises Kubota's medium and/or a hormonally defined medium (HDM) for the differentiation of cells.

Viability of thawed cells can be assessed in vitro as well as in vivo using various methods known in the art. In some embodiments, the in vitro cell viability tests includes the Trypan Blue exclusion assay. In some embodiments, other analytical methods can be used to assess the cell viability of thawed cells that had been frozen with the different cryopreservation medium, for example, gene expression, through the use of RT-qPCR and the like. A person of ordinary skill in the art can opt for any analytical method to assess the viability of thawed cells that can be applied to assess the cell viability of otherwise fresh cells.

Viability of cells in vivo, in general, can be assessed by evaluating the functional characteristics of administered cells in vivo. In some embodiments, the in vivo viability of cells can be assessed by evaluating the cell number of the cells that have been introduced into a subject in need. Various methods are known in the art for tracing cells and determining viability of administered cells.

The cryopreserved and thawed cells using the cryopreservation media described herein allows for using the cells for any purpose that a primary cell or fresh cell isolate can have. The cryopreserved and thawed cells retain high viability (e.g., greater than 70%, 75%, 80%, 85%, 90%, 95%, or greater than 95%) and retain physiological characteristics of their native state, which allows the cells to be used for a variety of applications, such as for genetic manipulation of the cells, and for cell therapy purposes such as, for example, in adoptive cell therapy applications.

```
Sequences disclosed herein:
Anti-CD19 Light chain variable fragment, VL:
                                        (SEQ ID NO: 1)
DIQMTQTTSSLSASLGDRVTISCRASQDISKYLNWYQQKPDGTVKLLIY

HTSRLHSGVPSRFSGSGSGTDYSLTISNLEQEDIATYFCQQGNTLPYTF

GGGTKLELKR

Anti-CD19 Heavy chain variable fragment, VH:
                                        (SEQ ID NO: 2)
EVQLQQSGPGLVAPSQSLSVTCTVSGVSLPDYGVSWIRQPPRKGLEWLG

VIWGSETTYYNSALKSRLTIIKDNSKSQVFLKMNSLQTDDTAIYYCAKH

YYYGGSYAMDYWGQGTTVTVSSYVTVSSQDPA

CD28:
                                        (SEQ ID NO: 3)
FWVLVVVGGVLACYSLLVTVAFIIFWVRSKRSRLLHSDYMNMTPRRPGP

TRKHYQPYAPPRDFAAYRS

CD3ζ:
                                        (SEQ ID NO: 4)
RVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATK

DTYDALHMQALPPRGP
```

EXAMPLES

Other features, objects, and advantages of the present invention are apparent in the examples that follow. It should be understood, however, that the examples, while indicating embodiments of the present invention, are given by way of illustration only, not limitation. Various changes and modifications within the scope of the invention will become apparent to those skilled in the art from the examples.

The NK cells used in these examples comprise anti-CD19 CAR, IL-15 and iCaspase9. However, it should be noted that NK cells comprising other transgenes can also be used with these methods.

The CAR-NK cells used in these examples were cord blood unit-derived NK cells that were transduced with genes encoding a tumor targeting CD19-CAR (iC9/CAR.19/IL15). Cord blood (CB) and peripheral blood monocytes (PBMCs) were isolated by a density-gradient technique. CD56+NK cells, purified with an NK isolation kit, were stimulated with irradiated (100 Gy) Clone 9.mbIL21 cells which co-express CD64/FcTRI, CD86/B7-2, CD137L/4-1BBL, truncated CD19,_and membrane-bound IL-21 reported to promote peripheral blood and CB NK cell expansion (2:1 feeder cell: NK ratio) and recombinant human IL-2 in complete Serum-free Stem Cell Growth Medium on day 0. Activated NK cells were transduced with retroviral supernatants on day +4 in human fibronectin-coated plates. Five days later (day +9), NK cells were stimulated again with irradiated Clone 9 and IL-2. On day +14, CAR-transduced NK cells were harvested for use.

The CAR NK cells were transduced with a nucleic acid molecule encoding an anti-CD-19 binding domain light chain variable region comprising the amino acid sequence set forth in SEQ ID NO: 1 and/or encoding an anti-CD19 binding domain heavy chain variable region comprising the amino acid sequence set forth in SEQ ID NO: 2.

Example 1: Scale-Up of Cryopreservation of Mammalian Cells in 50 ml Container This Example shows freeze profile of mammalian cells using a 120 min freeze sequence.

First, 45 ml of cryopreservation medium without cells (control) were filled into a 50 ml AT vial, comprising 50% RPMI, 5% DMSO, 20% of 25% Human Serum Albumin, 10% Dextran in NaCl. The temperature of the vial was reduced to 4° C. in a CryoMed™ 5474 controlled freezing equipment. The amount of heat emitted by the contents of the AT-vial was measured by measuring solution temperature. To begin the process of cryopreservation, the temperature was lowered to −4° C. at a rate of 1° C. per minute. Next, the temperature was reduced to −45° C. rapidly, at a rate of 20° C. per minute. Next, the temperature was increased to −10° C. rapidly, at a rate of 10° C. per minute. Next, the temperature was reduced to −20° C. rapidly, at a rate of 0.5° C. per minute. Finally, the temperature was reduced to −80° C. slowly by reducing temperature at a rate of 1° C. per minute.

Figure 2:
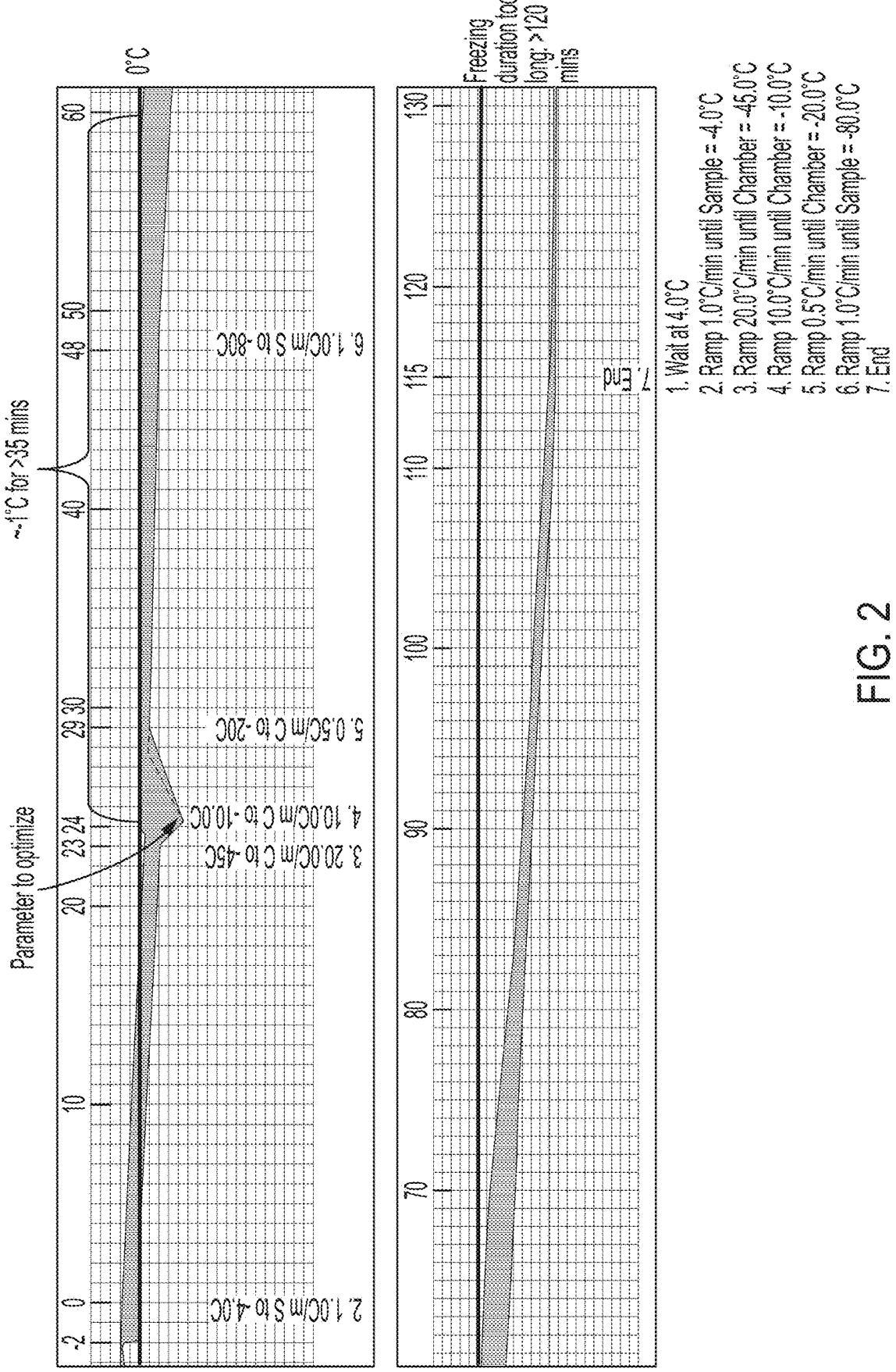
FIG. 2 is a graph showing the freeze profile of 45 ml of placebo formulation solution without cells using a freeze protocol for large volume, as described in Example 1.

It was observed that the amount of heat released by the contents of the solution remained at −1° C. for greater than 35 min with the freeze sequence, suggesting high chance of ice melting and slow ice formation. Further, the temperature of the contents of the vial were different from the temperature of the surrounding, also giving raise to high probability of non-uniform ice formation. FIG. 2 shows the freeze-profile of cryopreservation medium frozen using the above-mentioned freeze sequence.

Example 2: Optimized Cryopreservation of Mammalian Cells in 50 ml Container

This Example shows a method of cryopreservation of mammalian cells in a 50 ml container, such as 50 ml AT vials, such that the impact of latent heat of fusion is minimized.

First, 36 ml of CAR-NK cells were formulated in a media comprising 40% PLASMA-LYTE A +10% HSA+50% CS10 at a concentration of 110 million cells per mL and then filled into a 50 ml AT vial. The temperature of the vial was reduced to 4° C. in a controlled rate freezing device. For these experiments the CryoMed™ 5474 controlled rate freezing device was used. To begin the process of cryopreservation, the temperature was lowered to −2° C. at a rate of 1° C. per minute. The interior temperature of the vial and the contents were allowed to equilibrate at −2° C. for 3 minutes. The process of nucleation of ice was induced by reducing the temperature to −60° C. rapidly at a rate of 25° C. per minute. The interior of the vial and the contents of the vial were allowed to equilibrate at −60° C. for 1 minute to absorb latent heat of fusion due to initiation of ice formation to maintain cell suspension temperature below freezing point to avoid ice re-melting. To avoid expedited extracellular ice formation resulting in undesirable intracellular ice formation, the temperature was raised to −30° C. at a rate of 10° C. per minute to enable a continuous smooth temperature drop to enable gradual extracellular ice formation while intracellular water continued to osmotically move out. The temperature was held at −30° C. to allow uniform freezing of cells. Finally, the temperature was lowered to −40° C. at a rate of 1° C. per minute. The contents of the cells were equilibrated at −40° C. for 5 minutes to maximize extracellular ice formation. The temperature was lowered to the final temperature of −80° C., at a rate of 10° C. per minute to enable any residual extracellular ice formation. The amount of heat released by the samples and chamber temperature and system temperatures were plotted as a function of time. FIG. 3 shows the freezing profile of CAR-NK cells.

It was observed that the amount of heat released by the contents of the cells remained nearly constant throughout the freezing protocol, suggesting significant reduction in the latent heat of fusion. Further, the time taken for the thawing sequence less than 1 hour.

Example 3: Cryopreservation of Mammalian Cells in Multiple 50 ml Containers

This Example shows a method of cryopreservation of mammalian cells (e.g., cells suitable for cell therapy) in five 50 ml containers, such as 50 ml AT vials, arranged at four corners and center, such that the impact of latent heat of fusion was minimized.

First, five containers comprising 45 ml of iCAR-T cells in an appropriate cryopreservation suspension medium were provided containing cells at a concentration of 80 million cells/ml in a 50 ml AT vial. The temperature of the vial was reduced to 4° C. in a CryoMed™ 5474 controlled freezing equipment. To begin the process of cryopreservation, the temperature was lowered to −2° C. at a rate of 1° C. per minute. The interior temperature of the vial and the contents were allowed to equilibrate at −2° C. for 3 minutes. The process of nucleation of ice was started by reducing the temperature to −60° C. rapidly at a rate of 25° C. per minute. The interior of the vial and the contents of the vial were allowed to equilibrate at −60° C. for 1 minute to absorb latent heat of fusion due to initiation of ice formation to maintain cell suspension temperature below freezing point to avoid ice re-melting. To avoid expedited extracellular ice formation resulting in undesirable intracellular ice formation, the temperature was raised to −30° C. at a rate of 10° C. per minute to enable a continuous smooth temperature drop to enable gradual extracellular ice formation while intracellular water continued to osmotically move out. The temperature was held at −30° C. to allow uniform freezing of cells. Finally, the temperature was lowered to −40° C. at a rate of 1° C. per minute. The contents of the cells were equilibrated at −40° C. for 5 minutes to maximize extracellular ice formation. The temperature was lowered to the final temperature of −80° C., at a rate of 10° C. per minute to enable any residual extracellular ice formation. The amount of heat released by the samples and chamber temperature and system temperatures were plotted as a function of time. FIG. 4 shows the freezing profile of five 45 ml suspensions of CAR-NK cells.

It was observed that the amount of heat released by the contents of all five 45 ml cell suspension remained nearly constant throughout the freezing protocol, suggesting significant reduction of impact of latent heat of fusion created by extracellular ice formation. Further, use of multiple chambers suggested that the freezing protocol can be scaled up for large quantities of mammalian cell suspensions.

Example 4: Thawing Cryopreserved Mammalian Cells

This Example shows a method of thawing mammalian cells stored at liquid nitrogen temperatures (−196° C.) to reduce lethal ice recrystallization. The viability of thawed cells were measured.

iCART cells at cell densities of 80 million cells per ml, and 120 cells/ml taken in three different volumes, 16, 30 and 45 mL, in 50 ml AT vials, were initially cryopreserved using a method to reduce latent heat of fusion and frozen in 50 mL filled to in AT vials, and stored at −196° C. The cells stored at −196° C. were thawed by placing the AT vials in orbital shaker water bath (Benchmark SBL-12) set at 60° C., and at rotational speed of 120 rpm for up to 600 seconds. The temperature of the cell sample was measured. FIG. 5A and FIG. 5B show the increase in temperature of the cell sample with time during the thaw of 50 ml AT vials comprising 16, 30 and 45 ml of cells.

The viability of thawed cells were assessed. FIG. 6 shows the viability of 80 million cells per ml, and 120 million cells per ml thawed as described. It was observed that the all cells possessed greater than 95% viability, indicating that this method was successful in prevention of induction of lethal ice recrystallization.

Example 5: In Vitro Efficacy of Freezing and Thawing CAR-NK Cells

This example shows the efficacy of freezing and thawing mammalian CAR-NK cells in 50 mL AT vials as compared to 2 mL AT vials or 2 ml cryovials, when the mammalian cells were frozen in a method to minimize latent heat of fusion.

First, 45 mL, 30 mL and 10 mL of CAR-NK cells were taken in 50 mL AT vials at the concentration of 80 million and 120 million cells per mL. Next, 1 mL of CAR-NK cells were provided in 2 mL AT vials at 80 million and 120 million cells per mL or in 2 mL cryovials at concentration of 10 million cells per mL as control. All cells were suspended, in a cryopreservation suspension medium, comprising 40% PLASMA-LYTE A, 50% CS10, 10% Human Serum Albumin.

The CAR-NK cells filled into 50 mL and 2 mL AT vials were frozen as follows: the temperature of the vial was reduced to 4° C. and in a CryoMed™ 5474 controlled freezing equipment. To begin the process of cryopreservation, the temperature was lowered to −2° C. at a rate of 1° C. per minute. The interior temperature of the vial and the contents were allowed to equilibrate at −2° C. for 3 minutes. The process of nucleation of ice was started by reducing the temperature to −60° C. rapidly at a rate of 25° C. per minute. The interior of the vial and the contents of the vial were allowed to equilibrate at −60° C. for 1 minute to absorb latent heat of fusion due to initiation of ice formation to maintain cell suspension temperature below freezing point to avoid ice re-melting. To avoid expedited extracellular ice formation resulting in undesirable intracellular ice formation, the temperature was raised to −30° C. at a rate of 10° C. per minute to enable a continuous smooth temperature drop to enable gradual extracellular ice formation while intracellular water continued to osmotically move out. The temperature was held at −30° C. to allow uniform freezing of cells. Finally, the temperature was lowered to −40° C. at a rate of 1° C. per minute. The contents of the cells were equilibrated at −40° C. for 5 minutes to maximize extracellular ice formation. The temperature was lowered to the final temperature of −80° C., at a rate of 10° C. per minute to enable any residual extracellular ice formation. The CAR-NK cells in 2 mL cryovials were divided into two groups, one group were frozen using the benchmark program as frozen control and one group cultured in culture medium as fresh control.

The frozen cells were stored in the vapor phase of liquid nitrogen tank (<−140° C.) before thawing. The 50 mL and 2 mL AT vials were thawed by placing the AT vials in orbital shaker water bath (Benchmark SBL-12) set at 60° C., and at rotational speed of 150 rpm for up to 600 seconds. The cells frozen in 2 ml cryovials, were thawed at 37° C. in orbital shaker water bath (Benchmark SBL-12) set at 37° C., and at rotational speed of 150 rpm for up to 600 seconds The viability of cells was measured. The functionality of the cells were tested by measuring the percent killing of the CAR-NK cells at different E:T ratios. A 10:1 ratio of E:T was deemed as the best ratio for killing function comparison. Table 1 shows the viability and functional assays of CAR-NK cells. It was observed that greater than 93% of cells were viable as measured by measuring the number of stained dead cells and viable cells. Furthermore, it was observed the cells in 50 mL vials using the freeze and thaw sequence described herein demonstrated comparable viability, as the fresh cells and the cells with benchmark freeze and thaw method in their killing function (FIG. 7A). Further, the CAR-NK cells in 50 mL vials using the freeze and thaw sequence described herein demonstrated comparable immunophenotypes (Table 2) and fresh cells. FIG. 7A shows the percentage of killing by the CAR-NK cells as a function of E:T ratio. Table 2 shows the preservation of immunophenotypes in CAR-NK cells frozen and thawed.

TABLE 1

In vitro functional data, killing and viability of CAR-NK cells frozen
and thawed in 50 ml containers versus 2 ml vials.

| Sample | Container type | Cell Concentration. | Fill vol (ml) | % killing @ E:T = 10:1 | Frozen/ Fresh* | Viability |
|---|---|---|---|---|---|---|
| 1 | 50 ml AT | 120 M/ml | 16 | 87.2 | 1.04 | 93.8 |
| 2 | 50 ml AT | 120 M/ml | 30 | 86.6 | 1.03 | 93.9 |
| 3 | 50 ml AT | 120 M/ml | 45 | 86.9 | 1.03 | 93.8 |
| 4 | 2 mL AT | 120 M/mL | 1.0 | 79.7 | 0.95 | 93.7 |
| 5 | 50 ml AT | 80 M/ml | 16 | 87.2 | 1.04 | 94.0 |
| 6 | 50 ml AT | 80 M/ml | 30 | 87.7 | 1.04 | 94.5 |
| 7 | 50 ml AT | 80 M/ml | 45 | 86.5 | 1.03 | 94.1 |
| 8 | 2 mL AT | 80 M/mL | 1.0 | 82.7 | 0.98 | 93.9 |
| Fresh Cells | | | | 84.0 | 1.00 | 98.4 |
| Frozen cells | 2 mL cryovial | 10 M/mL | 1 mL | 84.0 | 1.00 | 98.7 |

*Note the Frozen/Fresh column values was obtained from normalizing the % killing of Frozen vs Fresh NK cells obtained from the same patient

TABLE 2

Shows preservation of immunophenotypes in CAR-NK cells frozen and thawed in 50 mL vials using the freeze and thaw
method described herein

| Reportable Marker | Batch Analytics Description | Statistic | CAR-NK-1 16 mL fill | CAR-NK-2 30 mL fill | CAR-NK-3 45 mL fill | CAR-NK-4 1 mL fill | CAR-NK-5 16 mL fill | CAR-NK-6 30 mL fill | CAR-NK-7 45 mL fill | CAR-NK-8 1 mL fill | CAR-NK-9 UTD | CAR-NK-10 Fresh |
|---|---|---|---|---|---|---|---|---|---|---|---|---|
| CD56− CD48+CD32+ CD56+CD3− | CD56− (FITC+)(APC+) | Grandparent | 0.00 | 0.00 | 0.01 | 0.00 | 0.00 | 0.00 | 0.00 | 0.00 | 0.00 | 0.00 |
| CD56+CD3− | CD56+(PE− Cy7−) | Parent | 97.84 | 97.90 | 98.31 | 97.51 | 97.10 | 98.05 | 98.06 | 95.96 | 98.08 | 98.14 |
| CD3+ | (PE−Cy7+) | Parent | 0.05 | 0.07 | 0.01 | 0.12 | 0.09 | 0.07 | 0.06 | 0.10 | 0.05 | 0.05 |
| F(ab')2+(NK− CAR)+ | F(ab')2 | Grandparent | 50.64 | 49.07 | 50.48 | 48.20 | 50.50 | 50.19 | 51.25 | 48.60 | 1.51 | 47.93 |

Example 6: In Vivo Efficacy of Freezing and Thawing of CAR-NK Cells

This example shows the in vivo efficacy of freezing and thawing mammalian CAR-NK cells in 50 mL AT vials as compared to 2 mL AT vials or 2 ml generic cryovials, when the mammalian cells were frozen in a method to minimize latent heat of fusion. AT cryovials are propriety cryovials that have specialized container closure technology.

First, 35 ml of CAR-NK cells were frozen in 50 ml AT vials at a concentration of 80 million cells per mL. The temperature of the vial was reduced to 4° C. a in a Cryo-Med™ 5474 controlled freezing equipment. To begin the process of cryopreservation, the temperature was lowered to −2° C. at a rate of 1° C. per minute. The interior temperature of the vial and the contents were allowed to equilibrate at −2° C. for 3 minutes. The process of nucleation of ice was started by reducing the temperature to −60° C. rapidly at a rate of 25° C. per minute. The interior of the vial and the contents of the vial were allowed to equilibrate at −60° C. for 1 minute to absorb latent heat of fusion due to initiation of ice formation to maintain cell suspension temperature below freezing point to avoid ice re-melting. To avoid expedited extracellular ice formation resulting in undesirable intracellular ice formation, the temperature was raised to −30° C. at a rate of 10° C. per minute to enable a continuous smooth temperature drop to enable gradual extracellular ice formation while intracellular water continued to osmotically move out. The temperature was held at −30° C. to allow uniform freezing of cells. Finally, the temperature was lowered to −40° C. at a rate of 1° C. per minute. The contents of the cells were equilibrated at −40° C. for 5 minutes to maximize extracellular ice formation. The temperature was lowered to the final temperature of −80° C., at a rate of 10° C. per minute to enable any residual extracellular ice formation. Upon completion of freezing, the frozen vials were stored in vapor phase of liquid nitrogen tank. Table 3 shows the components of the cryopreservation medium.

TABLE 3

Exemplary components of cryopreservation medium.

| Components | Vendor |
|---|---|
| PLASMA-LYTE A | Baxter |
| 25% HSA | Shire |
| CryoStor ® CS10 | BioLife Solutions |
| Trehalose | J. T. Baker |

The cryopreserved cells were thawed by placing the AT vials in an orbital shaker water bath (Benchmark SBL-12) set at 60° C., and at rotational speed of 150 rpm for up to 600 seconds.

Frozen and thawed CAR-NK were tested for both in vitro viability, killing and immunophenotypes. Further, the CAR-NK cells were injected into female NOD SCID Gamma (NSG) mice bearing luciferase expressing Raji human burkitt's lymphoma (Raji B.luc) xenografts. The NSG mice, female, 12-week-old were sourced from The Jackson Laboratory. The in vivo efficacy of freeze and thaw protocol in CAR-NK cells was measured by evaluating their in vivo kill efficacy in NOD/Shi-scid, IL-2R gamma null immunodeficient mice ("NSG mice"). Natural killing (NK) cell activation is an antigen-dependent process leading to proliferation and persistent of NK cells into effector cells. PBS was used as negative control.

The in vivo efficacy of CAR-NK cells were tested in female NOD SCID Gamma (NSG) mice bearing luciferase expressing Raji human burkitt's lymphoma (Raji B.luc) xenografts. One day before treatment (D minus 1) female NSG mice were randomized into groups with each group of 5 mice according to body weight and then received 1.5 Gray (1.5 Gy) of whole body irradiation. On Day 0, mice were co-administrated with $2 \times 10^4$ bioluminescent Raji B luc tumor cells and treatment via intravenous injection via tail vein. In vivo, luciferin was administered to the mice and whole body ventral images were captured nine minutes after substrate injection. Luciferase activity was measured in live mice using IVIS® Spectrum CT imaging system (PerkinElmer) post treatment. On the day of imaging, mice received luciferin substrate (150 mg/kg total; IP) injection and were placed in anesthesia induction chamber (2.5-3.5% isoflurane in oxygen). Upon sedation, mice were positioned in the imaging chamber for image acquisition nine minutes onwards post luciferin substrate injection.

FIG. 8 shows a graph of in vitro killing percent at different E:T ratios for the post thawing cells in 50 mL AT vials and 2 mL AT vials at both 6 million and 80 million cells in two cryopreservation medium, 40% PLASMA-LYTE A, 10% HSA, 50% CS10 with or without 30 mM trehalose. It was observed that frozen cells in 50 mL AT vials showed comparable killing function (FIG. 8). Table 4 summarizes the percent killing at 10:1 ratio of E:T and the percentage viability and recovery of CAR-NK cells frozen and thawed using the sequence described herein. It was observed that CAR-NK cells in 50 ml AT vials showed high and comparable viability (>97.0%) as the CAR-NK cells frozen in 2 ml AT vials. Table 5 summarizes the preservation of phenotypes in CAR-NK cells frozen in 50 ml vials versus 2 ml vials. It was observed that the immune phenotypes were preserved to the same degree in CAR-NK which were frozen in 50-ml AT vials as compared to CAR-NK cells frozen in 2 ml AT vials.

FIG. 9 further illustrates the in vivo efficacy of CAR-NK cells 36 days post-administration of CAR-NK cells. Three-different CAR-NK cells (e.g., obtained from different donors) were tested for in vivo efficacy. Two different formulations were used in these studies: 1) 40% PLASMA-LYTE A, 10% HSA, 50% CS10 (T6); and 2) 40% PLASMA-LYTE A, 10% HSA, 50% CS10, 30 mM Trehalose (T6T). The negative control mice were injected with media with cells (vehicle). It was observed that mice injected with NK-CAR cells showed less intense luciferase expression day 13/14 and day 20/21 (FIG. 9G-FIG. 9I). The total flux of luciferase fluorescence as a function of the time are shown in FIG. 9D-FIG. 9F. FIG. 9A-FIG. 9B show the percent survival of mice as a function of days after treatment. It was observed that mice injected with fresh CAR-NK cells and CAR-NK cells which were frozen and thawed according to the sequence described herein, showed comparable survival.

TABLE 4

Summary of percent viability, recovery and percent killing of CAR-NK cells in 50 mL AT vials as compared to 2 ml AT vials

| Sample | Container | Cell conc. | Fill vol (ml) | Formulation | % killing @ E:T = 10:1 | Viability (%) | % of Recovery |
|---|---|---|---|---|---|---|---|
| CAR-NK-1 | 50 mL AT vial | 6 M/mL | 35 | 40% PLASMA-LYTE A, 10% HSA, 50% CS10 | 93.01 | 97.3 | 100.2 |
| CAR-NK-2 | 2 mL AT vial | 80 M/mL | 1 | | 92.77 | 97.2 | 94.7 |
| CAR-NK-3 | 2 mL AT vial | 6 M/mL | 1 | | 89.76 | 96.6 | 109.5 |
| CAR-NK-4 | 50 mL AT vial | 6 M/mL | 35 | 40% PLASMA-LYTE A, 10% HSA, 50% CS10, 30 mM Trehalose | 92.17 | 97.7 | 106.5 |
| CAR-NK-5 | 2 mL AT vial | 80 M/mL | 1 | | 92.77 | 97.6 | 97.6 |
| CAR-NK-6 | 2 mL AT vial | 6 M/mL | 1 | | 91.69 | 98.3 | 109.1 |

TABLE 5

Summary of immunophenotype in CAR-NK cells

| Reportable Marker | Batch Analytics Description | Lineage | CAR-NK-DP-1 (50 ml AT) | CAR-NK-DP-2 (2 ml AT) | CAR-NK-DP-3 (2 ml AT) | CAR-NK-DP-4 (50 ml AT) | CAR-NK-DP-5 (2 ml AT) | CAR-NK-DP-6 (2 ml AT) |
|---|---|---|---|---|---|---|---|---|
| CD56− CD48+CD32+ | CD56− (FITC+)(APC+) | Grandparent | 0.00 | 0.00 | 0.00 | 0.00 | 0.00 | 0.00 |
| CD56+CD3− | CD56+ (PE−Cy7−) | Parent | 99.35 | 99.54 | 99.55 | 99.57 | 99.59 | 99.56 |
| CD3+ | (PE−Cy7+) | Parent | 0.09 | 0.07 | 0.11 | 0.12 | 0.12 | 0.12 |
| F(ab')2+(NK−CAR)+ | F(ab')2 | Grandparent | 72.45 | 72.82 | 72.28 | 72.98 | 72.55 | 73.19 |
| | | | 40% PLASMA-LYTE A, 10% HSA, 50% CS10 | | | 40% PLASMA-LYTE A, 10% HSA, 50% CS10, 30 mM Trehalose | | |

Example 7: Treating Subject in Need with CAR-NK Cells—Frozen, Shipped, Thawed, Administered with Vial This examples describes freezing, thawing and exemplary use of engineered CAR-NK cells as described herein. The exemplary use described in this example is the freezing, thawing and the administration of CAR NK cell to a cancer patient, such as a patient who has diffuse large B-cell lymphoma.

CAR-NK cells comprising CD19, IL-15 and iCaspase9 are suspended in a cryopreservation medium comprising human serum albumin (HSA), PLASMA-LYTE A, trehalose and CS10. The CAR-NK cells are frozen at a concentration of 6 M/mL to 25 M/mL in 50 mL cryovials at a fill sample fill volume of about 36 mL. One such cryovial can contain between 2 to 4 doses for a patient in need. The CAR-NK cells are frozen using the following freezing program comprising: (a) placing the sample at a first temperature above the freezing temperature of the sample; (b) reducing the first temperature to a second temperature at a first controlled rate, where the second temperature is at least 2° C. lower than the first temperature; (c) reducing the second temperature to a third temperature at a second controlled rate, where the third temperature is at least 40° C. lower than the second temperature; (d) increasing the third temperature to a fourth temperature at a third controlled rate, where the fourth temperature is at least 20° C. higher than the third temperature; (e) reducing the fourth temperature to a fifth temperature at a fourth controlled rate, where the fifth temperature is at least 10° C. lower than the fourth temperature; and (f) reducing the fifth temperature to the final temperature at a fifth controlled rate, where the final temperature is less than or equal to −80° C. Typically, the entire freezing process takes less than about 1 hour.

Once the cells are frozen, the sample is stored at a temperature of −140° C. or below. Such temperatures can be achieved in various manners, such as placement of the sample in liquid nitrogen vapor phase. The frozen can remain in storage stored at a temperature of −140° C. or below until needed for use. The time the cells can remain in storage for 1 week, 2 weeks, 1 month, 6 months, 1 year, 2 years, 5 years, 10 years or more.

Once the cells are needed for use, such as for example, for use in allogeneic cell therapy, the cells are transported from cryostorage to a hospital or other location in which a patient awaits transplant with the cells in a cryoshipper. During the shipping process, the cells are maintained at a temperature of −140° C. or below until then reach the hospital or other location (e.g., point of care). Once at the location, the cells are then thawed. The cells can be thawed as follows: heating a container comprising the cryopreserved engineered immune cells to a temperature of between 37° C. and 70° C.; and agitating the cells at a speed of between about 100 and about 250 RPM for a suitable period of time until the cells are thawed. The heating can be done, for example, at a temperature of between 60° C and 65° C. while agitating the sample of cells at a speed at between 100 and 125 RPM. The heating can either be performed using a water bath or using a dry heating device. Typically, the entire time to thaw the cells is about 10 minutes.

Thawing of the 50 mL cryovial can be performed at patient's bedside or other nearby location for easy access to the patient who will receive the cells. Once the sample is thawed, the total volume of the sample will be between about 34 to 36 mL. Up to about 34 mL of the thawed sample is administered into a patient using a vial adapter for aseptic administration. One thawed sample may contain multiple doses.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the following claims:

---

---

We claim:

1. A cell therapy composition comprising a population of natural killer (NK) cells in a cryopreservation medium comprising sodium chloride, sodium gluconate, sodium acetate trihydrate, potassium chloride, magnesium chloride, trehalose, dimethyl sulfoxide (DMSO) and human serum albumin, wherein the composition is thawed from a cryo-preserved state and is characterized by having greater than 90% cell viability.

2. The cell therapy composition of claim 1, wherein the trehalose is at a concentration of between about 10 mM-100 mM.

3. The cell therapy composition of claim 1, wherein the composition is characterized by having greater than 95% cell viability.

4. The cell therapy composition of claim 1, wherein the composition is characterized by having greater than 97% cell viability.

5. The cell therapy composition of claim 1, wherein the NK cells are present at 80-120 million cells per mL in the composition.

6. The cell therapy composition of claim 1, wherein the NK cells are present at 6 million cells per mL in the composition.

* * * * *

SEQUENCE LISTING

```
Sequence total quantity: 4
SEQ ID NO: 1              moltype = AA   length = 108
FEATURE                  Location/Qualifiers
REGION                   1..108
                         note = Anti-CD19 Light chain variable fragment, VL
source                   1..108
                         mol_type = protein
                         organism = synthetic construct
SEQUENCE: 1
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLELKR              108

SEQ ID NO: 2              moltype = AA   length = 130
FEATURE                  Location/Qualifiers
REGION                   1..130
                         note = Anti-CD19 Heavy chain variable fragment, VH
source                   1..130
                         mol_type = protein
                         organism = synthetic construct
SEQUENCE: 2
EVQLQQSGPG LVAPSQSLSV TCTVSGVSLP DYGVSWIRQP PRKGLEWLGV IWGSETTYYN  60
SALKSRLTII KDNSKSQVFL KMNSLQTDDT AIYYCAKHYY YGGSYAMDYW GQGTTVTVSS  120
YVTVSSQDPA                                                        130

SEQ ID NO: 3              moltype = AA   length = 68
FEATURE                  Location/Qualifiers
REGION                   1..68
                         note = CD28
source                   1..68
                         mol_type = protein
                         organism = synthetic construct
SEQUENCE: 3
FWVLVVVGGV LACYSLLVTV AFIIFWVRSK RSRLLHSDYM NMTPRRPGPT RKHYQPYAPP  60
RDFAAYRS                                                          68

SEQ ID NO: 4              moltype = AA   length = 114
FEATURE                  Location/Qualifiers
REGION                   1..114
                         note = CD3-zeta
source                   1..114
                         mol_type = protein
                         organism = synthetic construct
SEQUENCE: 4
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PRGP        114
```